US011182728B2

(12) United States Patent
Diaz et al.

(10) Patent No.: US 11,182,728 B2
(45) Date of Patent: Nov. 23, 2021

(54) MEDICATION WORKFLOW MANAGEMENT

(71) Applicant: CAREFUSION 303, INC., San Diego, CA (US)

(72) Inventors: Nivaldo Diaz, San Diego, CA (US); Guy Eldredge, Encinitas, CA (US); Thomas William Utech, Dallas, TX (US); Maria Consolacion Jaskela, San Rafael, CA (US); William Lee Webster, Rockwall, TX (US); Timothy W. Vanderveen, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 225 days.

(21) Appl. No.: 14/891,962

(22) PCT Filed: May 22, 2014

(86) PCT No.: PCT/US2014/039228
§ 371 (c)(1),
(2) Date: Nov. 17, 2015

(87) PCT Pub. No.: WO2014/190200
PCT Pub. Date: Nov. 27, 2014

(65) Prior Publication Data
US 2016/0140315 A1 May 19, 2016

Related U.S. Application Data

(63) Continuation of application No. 13/931,746, filed on Jun. 28, 2013, now Pat. No. 10,650,925, and a (Continued)

(51) Int. Cl.
*G16H 20/10* (2018.01)
*G06Q 10/08* (2012.01)
(Continued)

(52) U.S. Cl.
CPC ......... *G06Q 10/083* (2013.01); *G06Q 10/087* (2013.01); *G16H 20/10* (2018.01);
(Continued)

(58) Field of Classification Search
CPC   A61J 7/0076; A61J 7/0454; A61J 1/00; A61J 2205/60; G06Q 10/087;
(Continued)

(56) References Cited

U.S. PATENT DOCUMENTS 2,141,006 A   12/1938   Marinksky
3,724,455 A   4/1973   Unger
(Continued)

FOREIGN PATENT DOCUMENTS

CA   2472098 A1   7/2003
CA   2554903 A1   4/2005
(Continued)

OTHER PUBLICATIONS

Amanda Y. Leong, Mary Pederson, Optimising workflow processes in an advanced medication dispensary, Nov. 2018, Research in Social and Administrative Pharmacy, ScienceDirect, ELSEVIER, vol. 14, issue 11, pp. 1072-1079 (Year: 2017).*
(Continued)

*Primary Examiner* — Jonathan Ng
*Assistant Examiner* — Teresa S Williams
(74) *Attorney, Agent, or Firm* — Morgan, Lewis & Bockius LLP

(57) ABSTRACT

Methods for managing preparation, delivery, and recycling of a medication for a patient are provided. In one aspect, a method includes interfacing with a medication preparation component, an inventory management component, a delivery management component, and a medication recycling management component. The medication preparation component fulfills a plurality of medication orders based on a
(Continued)

first set of parameters. The medication preparation component cannot interface directly with the parameters for the other components. The method includes providing the medication preparation component the first set of parameters based on the parameters for the other components. In another aspect, a method includes receiving a plurality of medication orders, providing preparation instructions when a medication order cannot be fulfilled by unused medications, providing delivery instructions for the medications, and receiving delivery verifications. Machine-readable media are also provided.

12 Claims, 6 Drawing Sheets

Related U.S. Application Data continuation of application No. 13/901,497, filed on May 23, 2013, now Pat. No. 9,076,115, and a continuation of application No. 13/901,504, filed on May 23, 2013, now abandoned, and a continuation of application No. 13/901,501, filed on May 23, 2013, now Pat. No. 10,430,554, and a continuation of application No. 13/900,482, filed on May 22, 2013, now Pat. No. 10,380,326, and a continuation of application No. 13/900,493, filed on May 22, 2013, now Pat. No. 10,372,880, and a continuation of application No. 13/900,502, filed on May 22, 2013, now abandoned.

(60) Provisional application No. 61/827,419, filed on May 24, 2013.

(51) Int. Cl.
*H04L 12/825* (2013.01)
*H04L 29/06* (2006.01)

(52) U.S. Cl.
CPC .......... *H04L 47/25* (2013.01); *H04L 65/4084* (2013.01); *H04L 65/605* (2013.01)

(58) Field of Classification Search
CPC ........ G06Q 50/24; G06Q 10/08; G06Q 10/00; G07F 17/0092; G06F 19/3462; G06F 19/3456; G06F 19/3481; G16H 20/10; G16H 20/13
USPC ........................................................ 705/2, 3
See application file for complete search history.

(56) References Cited

U.S. PATENT DOCUMENTS

| | | |
|---|---|---|
| 3,831,006 A | 8/1974 | Chaffin, III et al. |
| 3,848,112 A | 11/1974 | Weichselbaum et al. |
| 3,872,448 A | 3/1975 | Mitchell, Jr. |
| 3,898,984 A | 8/1975 | Mandel et al. |
| 3,910,260 A | 10/1975 | Sarnoff et al. |
| 3,921,196 A | 11/1975 | Patterson |
| 3,970,996 A | 7/1976 | Yasaka et al. |
| 4,051,522 A | 9/1977 | Healy et al. |
| 4,135,241 A | 1/1979 | Stanis et al. |
| 4,164,320 A | 8/1979 | Irazoqui et al. |
| 4,216,462 A | 8/1980 | McGrath et al. |
| 4,237,344 A | 12/1980 | Moore |
| 4,315,309 A | 2/1982 | Coll |
| 4,321,461 A | 3/1982 | Walter, Jr. et al. |
| 4,360,125 A | 11/1982 | Martindale et al. |
| 4,373,527 A | 2/1983 | Fischell |
| 4,476,381 A | 10/1984 | Rubin |
| 4,604,847 A | 8/1986 | Moulding, Jr. et al. |
| 4,636,950 A | 1/1987 | Caswell et al. |
| 4,674,652 A | 6/1987 | Aten et al. |
| 4,676,776 A | 6/1987 | Howson |
| 4,688,026 A | 8/1987 | Scribner et al. |
| 4,695,954 A | 9/1987 | Rose et al. |
| 4,696,671 A | 9/1987 | Epstein et al. |
| 4,731,726 A | 3/1988 | Allen, III |
| 4,733,364 A | 3/1988 | Yamagata |
| 4,741,732 A | 5/1988 | Crankshaw et al. |
| 4,756,706 A | 7/1988 | Kerns et al. |
| 4,785,969 A | 11/1988 | McLaughlin |
| 4,788,449 A | 11/1988 | Katz |
| 4,803,625 A | 2/1989 | Fu et al. |
| 4,810,243 A | 3/1989 | Howson |
| 4,828,545 A | 5/1989 | Epstein et al. |
| 4,831,562 A | 5/1989 | McIntosh et al. |
| 4,835,372 A | 5/1989 | Gombrich et al. |
| 4,839,806 A | 6/1989 | Goldfischer et al. |
| 4,847,764 A * | 7/1989 | Halvorson ............ G06F 19/326 700/231 |
| 4,850,009 A | 7/1989 | Zook et al. |
| 4,853,521 A | 8/1989 | Claeys et al. |
| 4,855,909 A | 8/1989 | Vincent et al. |
| 4,857,713 A | 8/1989 | Brown |
| 4,857,716 A | 8/1989 | Gombrich et al. |
| 4,865,584 A | 9/1989 | Epstein et al. |
| 4,882,575 A | 11/1989 | Kawahara |
| 4,899,839 A | 2/1990 | Dessertine et al. |
| 4,916,441 A | 4/1990 | Gombrich |
| 4,918,604 A | 4/1990 | Baum |
| 4,925,444 A | 5/1990 | Orkin et al. |
| 4,942,544 A | 7/1990 | McIntosh et al. |
| 4,950,246 A | 8/1990 | Muller |
| 4,967,928 A | 11/1990 | Carter |
| 4,970,669 A | 11/1990 | McIntosh et al. |
| 4,978,335 A | 12/1990 | Arthur, III |
| 5,001,630 A | 3/1991 | Wiltfong |
| 5,006,699 A | 4/1991 | Felkner et al. |
| 5,036,462 A | 7/1991 | Kaufman et al. |
| 5,036,852 A | 8/1991 | Leishman |
| 5,041,086 A | 8/1991 | Koenig et al. |
| 5,072,383 A | 12/1991 | Brimm et al. |
| 5,077,666 A | 12/1991 | Brimm et al. |
| 5,078,683 A | 1/1992 | Sancoff et al. |
| 5,088,056 A | 2/1992 | McIntosh et al. |
| 5,088,981 A | 2/1992 | Howson et al. |
| 5,100,380 A | 3/1992 | Epstein et al. |
| 5,126,957 A | 6/1992 | Kaufman et al. |
| 5,142,484 A | 8/1992 | Kaufman et al. |
| 5,153,416 A | 10/1992 | Neeley |
| 5,153,827 A | 10/1992 | Coutre et al. |
| 5,164,575 A | 11/1992 | Neeley et al. |
| 5,166,498 A | 11/1992 | Neeley |
| 5,171,977 A | 12/1992 | Morrison |
| 5,181,910 A | 1/1993 | Scanlon |
| 5,190,522 A | 3/1993 | Woicicki et al. |
| 5,207,642 A | 5/1993 | Orkin et al. |
| 5,208,762 A | 5/1993 | Charhut et al. |
| 5,235,507 A | 8/1993 | Sackler et al. |
| 5,256,157 A | 10/1993 | Samiotes et al. |
| 5,258,906 A | 11/1993 | Kroll et al. |
| 5,265,010 A | 11/1993 | Evans-Paganelli et al. |
| 5,267,174 A | 11/1993 | Kaufman et al. |
| 5,291,399 A | 3/1994 | Chaco |
| 5,292,029 A | 3/1994 | Pearson |
| 5,307,263 A | 4/1994 | Brown |
| 5,312,334 A | 5/1994 | Hara et al. |
| 5,314,243 A | 5/1994 | McDonald et al. |
| 5,315,505 A | 5/1994 | Pratt et al. |
| 5,317,506 A | 5/1994 | Coutre et al. |
| H1324 H | 6/1994 | Dalke et al. |
| 5,331,547 A | 7/1994 | Laszlo |
| 5,356,378 A | 10/1994 | Doan |
| 5,367,555 A | 11/1994 | Isoyama |
| 5,368,554 A | 11/1994 | Nazarian et al. |
| 5,371,692 A | 12/1994 | Draeger et al. |
| 5,374,813 A | 12/1994 | Shipp |
| 5,376,070 A | 12/1994 | Purvis et al. |
| 5,378,231 A | 1/1995 | Johnson et al. |

(56) References Cited

U.S. PATENT DOCUMENTS

| | | |
|---|---|---|
| 5,382,232 A | 1/1995 | Hague et al. |
| 5,390,238 A | 2/1995 | Kirk et al. |
| 5,401,059 A | 3/1995 | Ferrario |
| 5,404,384 A | 4/1995 | Colburn et al. |
| 5,408,443 A | 4/1995 | Weinberger |
| 5,412,372 A | 5/1995 | Parkhurst et al. |
| 5,412,564 A | 5/1995 | Ecer |
| 5,416,695 A | 5/1995 | Stutman et al. |
| 5,456,691 A | 10/1995 | Snell |
| 5,460,605 A | 10/1995 | Tuttle et al. |
| 5,465,082 A | 11/1995 | Chaco |
| 5,472,614 A | 12/1995 | Rossi |
| 5,502,944 A | 4/1996 | Kraft et al. |
| 5,515,426 A | 5/1996 | Yacenda et al. |
| 5,522,798 A | 6/1996 | Johnson et al. |
| 5,533,079 A | 7/1996 | Colburn et al. |
| 5,536,084 A | 7/1996 | Curtis et al. |
| 5,538,006 A | 7/1996 | Heim et al. |
| 5,542,420 A | 8/1996 | Goldman et al. |
| 5,544,649 A | 8/1996 | David et al. |
| 5,544,661 A | 8/1996 | Davis et al. |
| 5,547,470 A | 8/1996 | Johnson et al. |
| 5,561,412 A | 10/1996 | Novak et al. |
| 5,562,232 A | 10/1996 | Pearson |
| 5,564,803 A | 10/1996 | McDonald et al. |
| 5,573,506 A | 11/1996 | Vasko |
| 5,582,593 A | 12/1996 | Hultman |
| 5,583,758 A | 12/1996 | McIlroy et al. |
| 5,592,374 A | 1/1997 | Fellegara et al. |
| 5,593,267 A | 1/1997 | McDonald et al. |
| 5,594,786 A | 1/1997 | Chaco et al. |
| 5,597,995 A | 1/1997 | Williams et al. |
| 5,601,445 A | 2/1997 | Schipper et al. |
| 5,622,429 A | 4/1997 | Heinze |
| 5,628,309 A | 5/1997 | Brown |
| 5,630,710 A | 5/1997 | Tune et al. |
| 5,633,910 A | 5/1997 | Cohen |
| 5,643,212 A | 7/1997 | Coutre et al. |
| 5,644,778 A | 7/1997 | Burks et al. |
| 5,645,531 A | 7/1997 | Thompson et al. |
| 5,651,775 A | 7/1997 | Walker et al. |
| 5,655,118 A | 8/1997 | Heindel et al. |
| 5,657,236 A | 8/1997 | Conkright |
| 5,658,250 A | 8/1997 | Blomquist et al. |
| 5,672,154 A | 9/1997 | Sillen et al. |
| 5,681,285 A | 10/1997 | Ford et al. |
| 5,683,367 A | 11/1997 | Jordan et al. |
| 5,685,844 A | 11/1997 | Marttila |
| 5,689,229 A | 11/1997 | Chaco et al. |
| 5,692,640 A | 12/1997 | Caulfield et al. |
| 5,699,038 A | 12/1997 | Ulrich et al. |
| 5,700,998 A | 12/1997 | Palti |
| 5,703,786 A | 12/1997 | Conkright |
| 5,704,352 A | 1/1998 | Tremblay et al. |
| 5,710,551 A | 1/1998 | Ridgeway |
| 5,712,913 A | 1/1998 | Chaum |
| 5,713,856 A | 2/1998 | Eggers et al. |
| 5,721,913 A | 2/1998 | Ackroff et al. |
| 5,733,259 A | 3/1998 | Valcke et al. |
| 5,737,539 A | 4/1998 | Edelson et al. |
| 5,738,102 A | 4/1998 | Lemelson |
| 5,752,235 A | 5/1998 | Kehr et al. |
| 5,758,095 A | 5/1998 | Albaum et al. |
| 5,758,096 A | 5/1998 | Barsky et al. |
| 5,760,704 A | 6/1998 | Barton et al. |
| 5,764,034 A | 6/1998 | Bowman et al. |
| 5,772,585 A | 6/1998 | Lavin et al. |
| 5,774,865 A | 6/1998 | Glynn |
| 5,781,442 A | 7/1998 | Engleson et al. |
| 5,790,409 A | 8/1998 | Fedor et al. |
| 5,795,327 A | 8/1998 | Wilson et al. |
| 5,803,906 A | 9/1998 | Pratt et al. |
| 5,807,321 A | 9/1998 | Stoker et al. |
| 5,807,336 A | 9/1998 | Russo et al. |
| 5,819,229 A | 10/1998 | Boppe |
| 5,822,418 A | 10/1998 | Yacenda et al. |
| 5,822,544 A | 10/1998 | Chaco et al. |
| 5,832,488 A | 11/1998 | Eberhardt |
| 5,833,599 A | 11/1998 | Schrier et al. |
| 5,842,173 A | 11/1998 | Strum et al. |
| 5,842,976 A | 12/1998 | Williamson |
| 5,845,253 A | 12/1998 | Rensimer et al. |
| 5,845,254 A | 12/1998 | Lockwood et al. |
| 5,845,255 A | 12/1998 | Mayaud |
| 5,845,264 A | 12/1998 | Nellhaus |
| 5,848,593 A | 12/1998 | McGrady et al. |
| 5,850,344 A | 12/1998 | Conkright |
| 5,852,408 A | 12/1998 | Christiansen et al. |
| 5,855,550 A | 1/1999 | Lai et al. |
| 5,867,821 A | 2/1999 | Ballantyne et al. |
| 5,871,465 A | 2/1999 | Vasko |
| 5,883,806 A | 3/1999 | Meador et al. |
| 5,885,245 A | 3/1999 | Lynch et al. |
| 5,894,273 A | 4/1999 | Meador et al. |
| 5,895,371 A | 4/1999 | Levitas et al. |
| 5,899,998 A | 5/1999 | McGauley et al. |
| 5,903,211 A | 5/1999 | Flego et al. |
| 5,905,653 A | 5/1999 | Higham et al. |
| 5,907,490 A | 5/1999 | Oliver |
| 5,911,132 A | 6/1999 | Sloane |
| 5,911,687 A | 6/1999 | Sato et al. |
| 5,912,818 A | 6/1999 | McGrady et al. |
| 5,920,054 A | 7/1999 | Uber, III |
| 5,920,263 A | 7/1999 | Huttenhoff et al. |
| 5,928,329 A | 7/1999 | Clark et al. |
| 5,930,145 A | 7/1999 | Yuyama et al. |
| 5,935,099 A | 8/1999 | Peterson et al. |
| 5,941,710 A | 8/1999 | Lampotang et al. |
| 5,942,986 A | 8/1999 | Shabot et al. |
| 5,950,630 A | 9/1999 | Portwood et al. |
| 5,950,632 A | 9/1999 | Reber et al. |
| 5,953,099 A | 9/1999 | Walach |
| 5,954,641 A | 9/1999 | Kehr et al. |
| 5,957,885 A | 9/1999 | Bollish et al. |
| 5,961,036 A | 10/1999 | Michael et al. |
| 5,961,446 A | 10/1999 | Beller et al. |
| 5,971,593 A | 10/1999 | McGrady |
| 5,985,371 A | 11/1999 | Fujioka et al. |
| 5,995,077 A | 11/1999 | Wilcox et al. |
| 6,000,828 A | 12/1999 | Leet |
| 6,003,006 A | 12/1999 | Colella et al. |
| 6,009,333 A | 12/1999 | Chaco |
| 6,017,318 A | 1/2000 | Gauthier et al. |
| 6,021,392 A | 2/2000 | Lester et al. |
| 6,024,699 A | 2/2000 | Surwit et al. |
| 6,032,155 A | 2/2000 | de la Huerga |
| 6,039,251 A | 3/2000 | Holowko et al. |
| 6,047,203 A | 4/2000 | Sackner et al. |
| 6,048,087 A | 4/2000 | Laurent et al. |
| 6,053,887 A | 4/2000 | Levitas et al. |
| 6,063,026 A | 5/2000 | Schauss et al. |
| 6,082,776 A | 7/2000 | Feinberg |
| 6,112,182 A | 8/2000 | Akers et al. |
| RE36,871 E | 9/2000 | Epstein et al. |
| 6,112,502 A * | 9/2000 | Frederick ............ G06F 19/3462 221/10 |
| 6,134,582 A | 10/2000 | Kennedy |
| 6,135,949 A | 10/2000 | Russo et al. |
| 6,202,923 B1 | 3/2001 | Boyer et al. |
| 6,228,057 B1 | 5/2001 | Vasko |
| 6,241,704 B1 | 6/2001 | Peterson et al. |
| 6,269,340 B1 | 7/2001 | Ford et al. |
| 6,282,441 B1 | 8/2001 | Raymond et al. |
| 6,290,681 B1 | 9/2001 | Brown |
| 6,292,698 B1 | 9/2001 | Duffin et al. |
| 6,302,844 B1 | 10/2001 | Walker et al. |
| 6,312,378 B1 | 11/2001 | Bardy |
| 6,314,556 B1 | 11/2001 | DeBusk et al. |
| 6,319,200 B1 | 11/2001 | Lai et al. |
| 6,322,502 B1 | 11/2001 | Schoenberg et al. |
| 6,338,007 B1 | 1/2002 | Broadfield et al. |
| 6,339,732 B1 | 1/2002 | Phoon et al. |
| 6,406,426 B1 | 6/2002 | Reuss et al. |
| 6,409,684 B1 | 6/2002 | Wilk |

(56) References Cited

U.S. PATENT DOCUMENTS

| | | |
|---|---|---|
| 6,421,650 B1 | 7/2002 | Goetz et al. |
| 6,493,747 B2 | 12/2002 | Simmon et al. |
| 6,519,569 B1 | 2/2003 | White et al. |
| 6,529,892 B1 | 3/2003 | Lambert |
| 6,540,672 B1 | 4/2003 | Simonsen et al. |
| 6,558,352 B1 | 5/2003 | Hogan |
| 6,571,128 B2 | 5/2003 | Lebel et al. |
| 6,581,606 B2 | 6/2003 | Kutzko et al. |
| 6,671,563 B1 | 12/2003 | Engelson et al. |
| 6,745,764 B2 | 6/2004 | Hickle |
| 6,757,898 B1 | 6/2004 | Ilsen et al. |
| 6,785,589 B2 | 8/2004 | Eggenberger et al. |
| 6,796,956 B2 | 9/2004 | Hartlaub et al. |
| 6,799,149 B2 | 9/2004 | Hartlaub |
| 6,847,861 B2 | 1/2005 | Lunak et al. |
| 6,856,247 B1 | 2/2005 | Wallace |
| 6,873,268 B2 | 3/2005 | Lebel et al. |
| 6,993,402 B2 | 1/2006 | Klass et al. |
| 7,034,691 B1 | 4/2006 | Rapaport et al. |
| 7,054,844 B2 | 5/2006 | Fletcher et al. |
| 7,060,059 B2 | 6/2006 | Keith et al. |
| 7,096,072 B2 | 8/2006 | Engleson et al. |
| 7,201,734 B2 | 4/2007 | Hickle |
| 7,204,823 B2 | 4/2007 | Estes et al. |
| 7,215,991 B2 | 5/2007 | Besson et al. |
| 7,229,430 B2 | 6/2007 | Hickle et al. |
| 7,230,529 B2 | 6/2007 | Ketcherside, Jr. et al. |
| 7,256,708 B2 | 8/2007 | Rosenfeld et al. |
| 7,263,492 B1 | 8/2007 | Suresh et al. |
| 7,379,885 B1 | 5/2008 | Zakim |
| 7,384,420 B2 | 6/2008 | Dycus et al. |
| 7,398,183 B2 | 7/2008 | Holland et al. |
| 7,421,709 B2 | 9/2008 | Watson et al. |
| 7,433,853 B2 | 10/2008 | Brockway et al. |
| 7,443,303 B2 | 10/2008 | Spear et al. |
| 7,471,994 B2 | 12/2008 | Ford et al. |
| 7,526,769 B2 | 4/2009 | Watts, Jr. et al. |
| 7,587,415 B2 | 9/2009 | Gaurav et al. |
| 7,612,679 B1 | 11/2009 | Fackler et al. |
| 7,649,454 B2 | 1/2010 | Singh et al. |
| 7,693,697 B2 | 4/2010 | Westenskow et al. |
| 7,734,478 B2 | 6/2010 | Goodall et al. |
| 7,769,601 B1 | 8/2010 | Bleser et al. |
| 7,771,385 B2 | 8/2010 | Eggers et al. |
| 7,771,386 B2 | 8/2010 | Eggers et al. |
| 7,776,031 B2 | 8/2010 | Hartlaub et al. |
| 7,787,946 B2 | 8/2010 | Stahmann et al. |
| 7,796,045 B2 | 9/2010 | Spear et al. |
| 7,835,927 B2 | 11/2010 | Schlotterbeck et al. |
| 7,847,970 B1 | 12/2010 | McGrady |
| 7,860,583 B2 | 12/2010 | Condurso et al. |
| 7,860,724 B2 | 12/2010 | Chudy et al. |
| 7,962,544 B2 | 6/2011 | Torok et al. |
| 7,970,550 B2 | 6/2011 | Arakelyan et al. |
| 7,983,995 B2 * | 7/2011 | Murphy .................. A61J 1/035 700/216 |
| 8,005,688 B2 | 8/2011 | Coffman et al. |
| 8,024,200 B2 | 9/2011 | Jennings et al. |
| 8,027,749 B2 | 9/2011 | Vahlberg et al. |
| 8,160,895 B2 | 4/2012 | Schmitt et al. |
| 8,197,437 B2 | 6/2012 | Kalafut et al. |
| 8,239,062 B2 | 8/2012 | Vahlberg et al. |
| 8,284,059 B2 * | 10/2012 | Ross .................. G06Q 10/087 340/10.1 |
| 8,291,337 B2 | 10/2012 | Garmin et al. |
| 8,321,236 B2 | 11/2012 | Goodall et al. |
| 8,340,792 B2 | 12/2012 | Condurso et al. |
| 8,606,596 B1 * | 12/2013 | Bochenko .............. G06Q 10/00 705/2 |
| 8,655,751 B2 | 2/2014 | Renz |
| 8,666,774 B1 | 3/2014 | Gonzales, Jr. et al. |
| 8,689,008 B2 | 4/2014 | Rangadass et al. |
| 2001/0037083 A1 | 11/2001 | Hartlaub et al. |
| 2001/0044731 A1 | 11/2001 | Coffman et al. |
| 2002/0010679 A1 | 1/2002 | Felsher |
| 2002/0013640 A1 | 1/2002 | Phoon et al. |
| 2002/0016568 A1 | 2/2002 | Lebel et al. |
| 2002/0016923 A1 | 2/2002 | Knaus et al. |
| 2002/0022973 A1 | 2/2002 | Sun et al. |
| 2002/0026223 A1 | 2/2002 | Riff et al. |
| 2002/0032582 A1 | 3/2002 | Feeney et al. |
| 2002/0035484 A1 | 3/2002 | McCormick |
| 2002/0038392 A1 | 3/2002 | De La Huerga |
| 2002/0042636 A1 | 4/2002 | Koshiol et al. |
| 2002/0046346 A1 | 4/2002 | Evans |
| 2002/0077849 A1 | 6/2002 | Baruch et al. |
| 2002/0087114 A1 | 7/2002 | Hartlaub |
| 2002/0116509 A1 | 8/2002 | DeLaHuerga |
| 2002/0120350 A1 | 8/2002 | Klass et al. |
| 2002/0169636 A1 | 11/2002 | Eggers et al. |
| 2002/0198624 A1 | 12/2002 | Greenwald et al. |
| 2003/0009244 A1 | 1/2003 | Engleson et al. |
| 2003/0018495 A1 | 1/2003 | Sussman |
| 2003/0036683 A1 | 2/2003 | Kehr et al. |
| 2003/0045858 A1 | 3/2003 | Struys et al. |
| 2003/0051737 A1 | 3/2003 | Hickle et al. |
| 2003/0063524 A1 | 4/2003 | Niemiec et al. |
| 2003/0069481 A1 | 4/2003 | Hervy et al. |
| 2003/0098991 A1 | 5/2003 | Laverty et al. |
| 2003/0105389 A1 | 6/2003 | Noonan et al. |
| 2003/0105555 A1 | 6/2003 | Lunak et al. |
| 2003/0106553 A1 | 6/2003 | Vanderveen |
| 2003/0114836 A1 | 6/2003 | Estes et al. |
| 2003/0121517 A1 | 7/2003 | McFarland |
| 2003/0129578 A1 | 7/2003 | Mault |
| 2003/0135087 A1 | 7/2003 | Hickle et al. |
| 2003/0135388 A1 | 7/2003 | Martucci et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0149599 A1 | 8/2003 | Goodall et al. |
| 2003/0156143 A1 | 8/2003 | Westenskow et al. |
| 2003/0158746 A1 | 8/2003 | Forrester |
| 2003/0163223 A1 | 8/2003 | Blomquist |
| 2003/0205897 A1 | 11/2003 | Kaufman |
| 2003/0236683 A1 | 12/2003 | Henderson et al. |
| 2004/0046020 A1 | 3/2004 | Andreasson et al. |
| 2004/0068229 A1 | 4/2004 | Jansen et al. |
| 2004/0073329 A1 | 4/2004 | Engleson et al. |
| 2004/0088187 A1 | 5/2004 | Chudy et al. |
| 2004/0107118 A1 | 6/2004 | Harnsberger et al. |
| 2004/0122702 A1 | 6/2004 | Sabol et al. |
| 2004/0122705 A1 | 6/2004 | Sabol et al. |
| 2004/0122719 A1 | 6/2004 | Sabol et al. |
| 2004/0122790 A1 | 6/2004 | Walker et al. |
| 2004/0128162 A1 | 7/2004 | Schlotterbeck et al. |
| 2004/0152622 A1 | 8/2004 | Keith et al. |
| 2004/0167465 A1 | 8/2004 | Mihai et al. |
| 2004/0167804 A1 | 8/2004 | Simpson et al. |
| 2004/0172283 A1 | 9/2004 | Vanderveen et al. |
| 2004/0172300 A1 | 9/2004 | Mihai et al. |
| 2004/0172302 A1 | 9/2004 | Martucci et al. |
| 2004/0176297 A1 | 9/2004 | Cheung et al. |
| 2004/0188998 A1 | 9/2004 | Henthorn |
| 2004/0193325 A1 | 9/2004 | Bonderud et al. |
| 2004/0193446 A1 | 9/2004 | Mayer et al. |
| 2004/0260478 A1 | 12/2004 | Schwamm |
| 2005/0010166 A1 | 1/2005 | Hickle |
| 2005/0010269 A1 | 1/2005 | Lebel et al. |
| 2005/0020996 A1 | 1/2005 | Hartlaub et al. |
| 2005/0021297 A1 | 1/2005 | Hartlaub |
| 2005/0022274 A1 | 1/2005 | Campbell et al. |
| 2005/0033606 A1 | 2/2005 | Miller |
| 2005/0049179 A1 | 3/2005 | Davidson et al. |
| 2005/0055242 A1 | 3/2005 | Bello et al. |
| 2005/0088296 A1 | 4/2005 | Lee |
| 2005/0096941 A1 * | 5/2005 | Tong .................. G06Q 50/22 705/2 |
| 2005/0097566 A1 | 5/2005 | Watts et al. |
| 2005/0107914 A1 | 5/2005 | Engleson et al. |
| 2005/0108057 A1 | 5/2005 | Cohen et al. |
| 2005/0113945 A1 | 5/2005 | Engleson et al. |
| 2005/0119788 A1 | 6/2005 | Engleson et al. |
| 2005/0144043 A1 | 6/2005 | Holland et al. |

(56) References Cited

U.S. PATENT DOCUMENTS

| | | |
|---|---|---|
| 2005/0145010 A1 | 7/2005 | Vanderveen et al. |
| 2005/0148890 A1 | 7/2005 | Hastings |
| 2005/0171815 A1 | 8/2005 | Vanderveen |
| 2005/0224083 A1 | 10/2005 | Crass et al. |
| 2005/0278194 A1 | 12/2005 | Holland et al. |
| 2006/0026205 A1 | 2/2006 | Butterfield |
| 2006/0047538 A1 | 3/2006 | Condurso et al. |
| 2006/0053036 A1 | 3/2006 | Coffman et al. |
| 2006/0079831 A1 | 4/2006 | Gilbert |
| 2006/0101072 A1 | 5/2006 | Busche et al. |
| 2006/0122481 A1 | 6/2006 | Sievenpiper et al. |
| 2006/0122729 A1 | 6/2006 | Murphy et al. |
| 2006/0149416 A1 | 7/2006 | Mohapatra et al. |
| 2006/0178812 A1 | 8/2006 | Affleck et al. |
| 2006/0190302 A1 | 8/2006 | Eggers et al. |
| 2006/0200369 A1 | 9/2006 | Batch et al. |
| 2006/0206356 A1 | 9/2006 | Vanderveen |
| 2006/0217628 A1 | 9/2006 | Huiku |
| 2006/0218015 A1 | 9/2006 | Walker et al. |
| 2006/0229551 A1 | 10/2006 | Martinez et al. |
| 2006/0249423 A1 | 11/2006 | Reijonen |
| 2006/0271401 A1 | 11/2006 | Lassetter et al. |
| 2006/0287890 A1 | 12/2006 | Stead et al. |
| 2007/0015972 A1 | 1/2007 | Wang et al. |
| 2007/0043767 A1 | 2/2007 | Osborne et al. |
| 2007/0061266 A1 | 3/2007 | Moore et al. |
| 2007/0061393 A1 | 3/2007 | Moore |
| 2007/0083389 A1 | 4/2007 | Dyer et al. |
| 2007/0106457 A1 | 5/2007 | Rosenberg |
| 2007/0106753 A1 | 5/2007 | Moore |
| 2007/0106754 A1 | 5/2007 | Moore |
| 2007/0129647 A1 | 6/2007 | Lynn |
| 2007/0156452 A1 | 7/2007 | Batch |
| 2007/0156860 A1 | 7/2007 | Nedelcu et al. |
| 2007/0168301 A1 | 7/2007 | Eisner et al. |
| 2007/0185615 A1* | 8/2007 | Bossi ............... G06F 19/3462 700/244 |
| 2007/0208454 A1 | 9/2007 | Forrester et al. |
| 2007/0210157 A1 | 9/2007 | Miller |
| 2007/0286466 A1 | 12/2007 | Heffernan et al. |
| 2007/0293843 A1 | 12/2007 | Ireland et al. |
| 2008/0015549 A1 | 1/2008 | Maughan |
| 2008/0025230 A1 | 1/2008 | Patel et al. |
| 2008/0034323 A1 | 2/2008 | Blomquist |
| 2008/0040151 A1 | 2/2008 | Moore |
| 2008/0046292 A1 | 2/2008 | Myers et al. |
| 2008/0141272 A1 | 6/2008 | Borgendale et al. |
| 2008/0162254 A1 | 7/2008 | Herger et al. |
| 2008/0164998 A1 | 7/2008 | Scherpbier et al. |
| 2008/0169045 A1 | 7/2008 | Tribble et al. |
| 2008/0195246 A1 | 8/2008 | Tribble et al. |
| 2008/0195416 A1 | 8/2008 | Tribble et al. |
| 2008/0272138 A1 | 11/2008 | Ross et al. |
| 2008/0317672 A1 | 12/2008 | Viertio-Oja |
| 2008/0319795 A1 | 12/2008 | Poteet et al. |
| 2009/0012812 A1 | 1/2009 | Rausch et al. |
| 2009/0012813 A1 | 1/2009 | Berzansky et al. |
| 2009/0043253 A1 | 2/2009 | Podaima |
| 2009/0043611 A1 | 2/2009 | Nadas et al. |
| 2009/0054754 A1 | 2/2009 | McMahon et al. |
| 2009/0099867 A1 | 4/2009 | Newman |
| 2009/0112333 A1 | 4/2009 | Sahai |
| 2009/0125335 A1 | 5/2009 | Manetta et al. |
| 2009/0144078 A1 | 6/2009 | Bajars et al. |
| 2009/0150484 A1 | 6/2009 | Roberts |
| 2009/0210252 A1 | 8/2009 | Silver |
| 2009/0240651 A1 | 9/2009 | Fletcher et al. |
| 2009/0272677 A1 | 11/2009 | Mallett et al. |
| 2009/0306585 A1 | 12/2009 | Pang et al. |
| 2009/0306944 A1 | 12/2009 | Willmann et al. |
| 2009/0319623 A1 | 12/2009 | Srinivasan et al. |
| 2010/0037067 A1 | 2/2010 | Rangadass et al. |
| 2010/0042437 A1 | 2/2010 | Levy et al. |
| 2010/0082458 A1 | 4/2010 | Godlewski |
| 2010/0094653 A1 | 4/2010 | Tribble et al. |
| 2010/0121654 A1 | 5/2010 | Portnoy et al. |
| 2010/0161113 A1 | 6/2010 | Tribble et al. |
| 2010/0169120 A1 | 7/2010 | Herbst et al. |
| 2010/0169771 A1 | 7/2010 | Pelegrin et al. |
| 2010/0174552 A1 | 7/2010 | Hawkes et al. |
| 2010/0174553 A1 | 7/2010 | Kaufman et al. |
| 2010/0179825 A1 | 7/2010 | Hanov et al. |
| 2010/0241453 A1 | 9/2010 | Malec |
| 2010/0241456 A1 | 9/2010 | Miller et al. |
| 2010/0271218 A1 | 10/2010 | Hoag et al. |
| 2010/0280840 A1 | 11/2010 | Fukushi et al. |
| 2010/0323397 A1 | 12/2010 | Reavy et al. |
| 2011/0015941 A1 | 1/2011 | Backhaus |
| 2011/0046975 A1 | 2/2011 | Hoffman |
| 2011/0060758 A1 | 3/2011 | Schlotterbeck et al. |
| 2011/0078608 A1 | 3/2011 | Gannon et al. |
| 2011/0119612 A1 | 5/2011 | Gannon et al. |
| 2011/0179405 A1 | 7/2011 | Dicks et al. |
| 2011/0202495 A1 | 8/2011 | Gawlick |
| 2011/0257991 A1* | 10/2011 | Shukla ............... G06Q 50/22 705/2 |
| 2011/0282691 A1 | 11/2011 | Coffman et al. |
| 2011/0288882 A1 | 11/2011 | Halow |
| 2011/0313787 A1 | 12/2011 | Rangadass et al. |
| 2012/0011253 A1 | 1/2012 | Friedman et al. |
| 2012/0016215 A1 | 1/2012 | Condurso et al. |
| 2012/0041775 A1 | 2/2012 | Cosentino et al. |
| 2012/0053533 A1 | 3/2012 | Butterfield et al. |
| 2012/0075060 A1 | 3/2012 | Connor |
| 2012/0075061 A1 | 3/2012 | Barnes |
| 2012/0136673 A1 | 5/2012 | Presley et al. |
| 2012/0173254 A1 | 7/2012 | Korhnak et al. |
| 2012/0173264 A1 | 7/2012 | Brush et al. |
| 2012/0173391 A1 | 7/2012 | Korhnak et al. |
| 2012/0179006 A1 | 7/2012 | Jansen et al. |
| 2012/0182939 A1 | 7/2012 | Rajan et al. |
| 2012/0185267 A1 | 7/2012 | Kamen et al. |
| 2012/0185277 A1 | 7/2012 | Tribble et al. |
| 2012/0191052 A1 | 7/2012 | Rao |
| 2012/0205441 A1 | 8/2012 | Utech et al. |
| 2012/0239422 A1 | 9/2012 | Chudy et al. |
| 2012/0239824 A1 | 9/2012 | Nguyen et al. |
| 2012/0241043 A1 | 9/2012 | Perazzo et al. |
| 2012/0247480 A1 | 10/2012 | Varga |
| 2012/0253835 A1 | 10/2012 | Tracy et al. |
| 2012/0265549 A1 | 10/2012 | Virolainen |
| 2013/0006652 A1 | 1/2013 | Vahlberg et al. |
| 2013/0018356 A1 | 1/2013 | Prince et al. |
| 2013/0085771 A1 | 4/2013 | Ghanbari et al. |
| 2013/0096444 A1 | 4/2013 | Condurso et al. |
| 2013/0197927 A1 | 8/2013 | Vanderveen et al. |
| 2013/0197928 A1 | 8/2013 | Vanderveen et al. |
| 2013/0197929 A1 | 8/2013 | Vanderveen et al. |
| 2013/0197930 A1 | 8/2013 | Garibaldi et al. |
| 2013/0197931 A1 | 8/2013 | Gupta et al. |
| 2013/0204433 A1 | 8/2013 | Gupta et al. |
| 2013/0204637 A1 | 8/2013 | Vanderveen et al. |
| 2013/0226600 A1 | 8/2013 | Barfield |
| 2013/0262138 A1 | 10/2013 | Jaskela et al. |
| 2013/0282401 A1* | 10/2013 | Summers ............ G06F 19/3456 705/3 |
| 2014/0028464 A1 | 1/2014 | Garibaldi |
| 2014/0100868 A1 | 4/2014 | Condurso et al. |
| 2014/0278466 A1 | 9/2014 | Simmons et al. |
| 2014/0297313 A1 | 10/2014 | Condurso et al. |
| 2014/0350950 A1 | 11/2014 | Jaskela et al. |
| 2015/0250948 A1 | 9/2015 | Gupta et al. |
| 2016/0000997 A1 | 1/2016 | Batch et al. |

FOREIGN PATENT DOCUMENTS

| | | |
|---|---|---|
| CN | 1421810 A | 6/2003 |
| CN | 1759398 A | 4/2006 |
| CN | 101116077 A | 1/2008 |
| CN | 101146055 A | 3/2008 |
| CN | 201110955 Y | 9/2008 |
| CN | 101331491 A | 12/2008 |
| CN | 101689320 A | 3/2010 |
| CN | 101890193 A | 11/2010 |

(56) References Cited

FOREIGN PATENT DOCUMENTS

| | | |
|---|---|---|
| CN | 102068725 A | 5/2011 |
| CN | 10 2521394 A | 6/2012 |
| CN | 102508877 A | 6/2012 |
| CN | 102688532 A | 9/2012 |
| CN | 102799783 A | 11/2012 |
| DE | 4023785 A1 | 1/1992 |
| EP | 0192786 A2 | 9/1986 |
| EP | 0384155 A2 | 8/1990 |
| EP | 0595474 A2 | 5/1994 |
| EP | 0649316 A1 | 4/1995 |
| EP | 0652528 A2 | 5/1995 |
| EP | 0784283 A1 | 7/1997 |
| EP | 0921488 A1 | 6/1999 |
| EP | 1003121 A2 | 5/2000 |
| EP | 1018347 A2 | 7/2000 |
| EP | 1237113 A2 | 9/2002 |
| EP | 1750573 A1 | 2/2007 |
| GB | 2 141 006 A | 12/1984 |
| JP | 62114562 | 5/1987 |
| JP | 11505352 | 5/1999 |
| JP | 2002520718 A | 7/2002 |
| JP | 2003085283 A | 3/2003 |
| JP | 2004287616 A | 10/2004 |
| JP | 2005165442 A | 6/2005 |
| JP | 2005296428 A | 10/2005 |
| JP | 2006155070 A | 6/2006 |
| JP | 2006521183 A | 9/2006 |
| JP | 2008508616 A | 3/2008 |
| JP | 2008516303 A | 5/2008 |
| JP | 2011501311 A | 1/2011 |
| JP | 2012200430 A | 10/2012 |
| JP | 5168708 B2 | 3/2013 |
| KR | 1020070045611 | 5/2007 |
| KR | 100738253 B1 | 7/2007 |
| KR | 1020080013129 | 2/2008 |
| KR | 100847397 B1 | 7/2008 |
| KR | 1020100049549 | 5/2010 |
| KR | 1020100125972 | 12/2010 |
| KR | 1020110070824 | 6/2011 |
| KR | 20120070045 A | 6/2012 |
| KR | 1020120076615 | 7/2012 |
| KR | 1020120076635 | 7/2012 |
| NZ | 522631 A | 7/2004 |
| WO | WO-1993022735 A1 | 11/1993 |
| WO | WO-1994005344 A1 | 3/1994 |
| WO | WO-1994008647 A1 | 4/1994 |
| WO | WO-1994013250 A1 | 6/1994 |
| WO | WO-1995023378 A2 | 8/1995 |
| WO | WO-1996020745 A1 | 7/1996 |
| WO | WO-1996025214 A1 | 8/1996 |
| WO | WO-1996036923 A1 | 11/1996 |
| WO | WO-1997004712 A1 | 2/1997 |
| WO | WO-1998013783 A1 | 4/1998 |
| WO | WO-1998028676 A2 | 7/1998 |
| WO | WO-1999009505 A1 | 2/1999 |
| WO | WO-1999010829 A1 | 3/1999 |
| WO | WO-1999010830 A1 | 3/1999 |
| WO | WO-1999035588 A1 | 7/1999 |
| WO | WO-1999044167 A1 | 9/1999 |
| WO | WO-1999045490 A2 | 9/1999 |
| WO | WO-1999046718 A1 | 9/1999 |
| WO | WO-1999067732 A1 | 12/1999 |
| WO | WO-2000003344 | 1/2000 |
| WO | WO-2000004521 | 1/2000 |
| WO | WO-2000018449 | 4/2000 |
| WO | WO-2000032088 | 6/2000 |
| WO | WO-2000032098 | 6/2000 |
| WO | WO-200139874 | 6/2001 |
| WO | WO-2001086506 | 11/2001 |
| WO | WO-2001088828 | 11/2001 |
| WO | WO-2002036044 | 5/2002 |
| WO | WO-2002069099 | 9/2002 |
| WO | WO-2003038566 | 5/2003 |
| WO | WO-2003053503 | 7/2003 |
| WO | WO-2003092769 | 11/2003 |
| WO | WO-2003094091 | 11/2003 |
| WO | WO-2004060443 A2 | 7/2004 |
| WO | WO-2004061745 A2 | 7/2004 |
| WO | WO-2002053209 A1 | 10/2004 |
| WO | WO2006055515 * | 11/2004 ............... A61J 1/03 |
| WO | WO-2005110208 A1 | 11/2005 |
| WO | WO-2008087982 A1 | 5/2010 |
| WO | WO-2010124016 A1 | 10/2010 |
| WO | WO-2010124328 A1 | 11/2010 |
| WO | WO-2011054712 A1 | 5/2011 |
| WO | WO-2012095829 A2 | 7/2012 |
| WO | WO-2014159280 A1 | 10/2014 |

OTHER PUBLICATIONS

U.S. Appl. No. 90/009,912, filed Aug. 12, 2013, Schlotterbeck et al.
U.S. Appl. No. 90/011,697, filed Aug. 12, 2013, Schlotterbeck et al.
"General-Purpose Infusion Pumps," Evaluation—Health Devices, Oct. 2002, pp. 353-387, vol. 31 (10), ECRI Institute.
"Infusion Pump Technology," Health Devices, Apr.-May 1998, pp. 150-170, vol. 27(4-5), ECRI Institute.
"Infusion Pumps, General Purpose," Healthcare Product Comparison System, 2007, pp. 1-54, ECRI Institute.
"Infusion Pumps, Large-Volume," Healthcare Product Comparison System, 2010, pp. 1-51, ECRI Institute.
"Introducing DoseEdge Pharmacy Workflow Manager", Baxter Healthcare Corporation, visisted May 22, 2013, retrieved from <http://baxa.com/doseedge/>.
"Pandora Analytics", Pandora Healthcare Data Analytics by Omnicell, retrieved from <http://www.omnicell.com/Products/Business_Analytics/Pandora_Analytics.aspx>, retrieved Jul. 10, 2013, pp. 1-4, Omnicell, Inc.
"Smart Infusion Pumps Join CPOE and Bar Coding as Important Ways to Prevent Medication Errors," ISMP—Medication Safety Alert, Feb. 7, 2002, 2 pgs., Institute for Safe Medication Practices.
"Welcome to Medacist Solutions Group, LLC", Medacist—The Key to Healthcare Automation, retrieved from <http://www.medacist.com>, retrieved Jul. 10, 2013, 1 page, Medacist Solutions Group, LLC.
Anonymous, "Pyxis MedStation™ 4000 System. Console User Guide" In: "Part No. 127157-06", Nov. 1, 2010, Cardinal Health, XP055121062, pp. 1-228, p. 21-22, p. 38-61, p. 123-125, p. 157-166, p. 200, p. 216.
Anonymous, Guardrails® Safety Software—Medley TM Medication Safety System, Alaris Medical Systems XP-00234431; 2002 Alaris Medical Systems Inc. 11/02, SSM @2159C.
Baldauf-Sobez et al., "How Siemens' Computerized Physician Order Entry Helps Prevent the Human Errors," electromedica, vol. 71, No. 1, 2003, pp. 2-10.
Calabrese, et al., "Medication administration errors in adult patients in the ICU," Intensive Care Med, 2001, pp. 1592-1598, vol. 27, Springer-Verlag.
Eskew, James et al., Using Innovative Technologies To Set New Safety Standards For The Infusion Of Intravenous Medications, Hospital Pharmacy, vol. 37, No. 11, pp. 1179-1189, 2002, Facts and Comparisons.
Extended European Search Report for Application No. 14779655.1, dated Jul. 14, 2016, 8 pages.
Extended European Search Report for Application No. 14780320.9, dated Jul. 1, 2016, 7 pages.
International Search Report and Written Opinion for PCT Application No. PCT/US2014/022830, dated Jun. 19, 2014, 6 pages.
International Search Report and Written Opinion for PCT Application No. PCT/US2014/022832, dated Jun. 24, 2014, 5 pages,.
International Search Report and Written Opinion for PCT Application No. PCT/US2014/022835.
International Search Report and Written Opinion for PCT Application No. PCT/US2014/022837, dated Jun. 18, 2014.
International Search Report and Written Opinion for PCT Application No. PCT/US2014/022840, dated Jun. 19, 2014, 5 pages.
International Search Report and Written Opinion for PCT Application No. PCT/US2014/037577 dated Sep. 5, 2014.

(56) References Cited

OTHER PUBLICATIONS

International Search Report and Written Opinion in International Patent Application No. PCT/US2014/012594 dated Jun. 11, 2014, 16 pages.
International Search Report and Written Opinion in PCT Application No. PCT/US2014/038498 dated Sep. 17, 2014.
International Search Report and Written Opinion in PCT Application No. PCT/US2014/038654 dated Oct. 7, 2014, 12 pages.
International Search Report and Written Opinion in PCT Patent Application No. PCT/US2014/039228 dated Aug. 22, 2014, 11 pgs.
International Search Report and Written Opinion of the International Searching Authority for PCT Application No. PCT/US2014/038658, dated Oct. 7, 2014.
International Search Report for Application No. PCT/US2014/038497, dated Oct. 23, 2014, 3 pages.
Kohn, et al., "To Err is Human—Building a Safer Health System," National Academy Press, 2002, pp. i-287, National Academy of Sciences.
Lesar, "Recommendations for Reducing Medication Errors," Medscape Pharamcists, posted Jul. 24, 2000, 10 pgs, vol. 1(2), Medscape Pharamcists, <http://www.medscape.com>.
Meier, "Hospital Products Get Seal of Approval at a Price," The New York Times, Apr. 23, 2002, 5 pgs.
Queensland Health. Use of returned or unused dispensed medicines, Jan. 5, 2005, Queensland Government. pp. 1-2.
Shabot et al., "Wireless clinical alerts for critical medication, laboratory and physiologic data," System Sciences 2000. Proceedings of the 33rd Annual Conference on Jan. 4-7, 2000, Piscataway, NJ, IEEE, Jan. 4, 2000.
Williams, et al., "Reducing the Risk of User Error with Infusion Pumps," Professional Nurse—Safe Practice—Infusion Devices, Mar. 2000, pp. 382-384, vol. 15(6).
Yokoi, "Prevention of Errors in Injection/Drip Infusion—No excuse for ignorance!—Essential Points of Accident Prevention, IV Infusion Pump, Syringe-pump Accident Prevention," JIN Special, Igaku Shoin K.K., Dec. 1, 2001, pp. 109-120, No. 70.
Canadian Office Action for Application No. 2551903, dated Mar. 28, 2017, 7 pages.
European Office Action for Application No. 12756903.6, dated Apr. 19, 2017, 5 pages.
Office Action for United Arab Emirates Application No. UAE/P/0962/2013, dated Apr. 17, 2017, 18 pages.
Chinese Office Action for Application No. 201480015147.6, dated Mar. 10, 2017, 10 pages excluding translation.
Australian Examination Report No. 1 for Application No. 2016216550, dated Sep. 20, 2017, 3 pages.
Chinese Office Action for Application No. 201480015147.6, dated Nov. 16, 2017, 8 pages.
European Communication of the Board of Appeal for Application No. 05791269.3, dated Nov. 10, 2017, 7 pages.
European Office Action for Application No. 14775918.7, dated Dec. 20, 2017, 8 pages.
Canadian Office Action for Application No. 2512991, dated Mar. 2, 2017, 4 pages.
Extended European Search Report for Application No. 14801726.2, dated Jan. 5, 2017, 8 pages.
Evans, R. S. et al., "Enhanced notification of infusion pump programming errors", Studies in health technology and informatics, Jan. 1, 2010, pp. 734-738, XP055305644, Netherlands DOI: 10.3233/978-1-60750-588-4-734 Retrieved from the Internet: URL:http://booksonline.iospress.nl/Extern/EnterMedLine.aspx?ISSN=0926-9630&Volume=160&SPage=734 [retrieved on Sep. 26, 2016].
Extended European Search Report and Written Opinion for Application No. 14772937.0, dated Oct. 10, 2016, 9 pages.
Extended European Search Report and Written Opinion for Application No. 14779139.6, dated Nov. 7, 2016, 7 pages.
European Office Action for Application No. 14779655.1, dated Jul. 28, 2017, 6 pages.
Memo concerning Mexican Office Action for Application No. MX/a/2015/015959, dated Sep. 21, 2017, 4 pages.
Extended European Search Report for Application No. 14801713.0, dated Jan. 16, 2017, 8 pages.
Extended European Search Report for Application No. 14775918.7, dated Sep. 13, 2016, 10 pages.
Canadian Office Action for Application No. 2551903, dated Mar. 5, 2018, 8 pages.
Chinese Office Action for Application No. 201480015147.6, dated May 3, 2018, 6 pages.
European Office Action for Application No. 14772937.0, dated Apr. 19, 2018, 9 pages.
Memo concerning Mexican Office Action for Application No. MX/a/2015/016104, memo dated May 4, 2018, 3 pages.
Australian Office Action for Application No. 2014268828, dated Jul. 26, 2019, 4 pages.
Chinese Office Action for Application No. 201480015025.7, dated Jun. 24, 2019, 25 pages.
Chinese Office Action for Application No. 201480015036.5, dated Jun. 24, 2019, 20 pages.
European Summons to attend oral proceedings pursuant to Rule 115(1) EPC for Application No. 14772937.0, dated Jul. 17, 2019, 12 pages.
Chinese Office Action for Application No. 201480015093.3, dated Apr. 25, 2019, 18 pages.
Chinese Office Action for Application No. 201480041985.0, dated Apr. 3, 2019, 12 pages.
Japanese Office Action for Application No. 2016-501081, dated May 7, 2019, 4 pages.
Australian Office Action for Application No. 2014241022, dated Feb. 7, 2019, 4 pages.
Australian Office Action for Application No. 2014241019, dated Feb. 6, 2019, 3 pages.
Chinese Office Action for Application No. 201480041362.3 dated Apr. 4, 2019, 19 pages.
Canadian Office Action for Application No. 2512991, dated Jan. 10, 2018, 4 pages.
Canadian Office Action for Application No. 2828898, dated Jan. 11, 2018, 8 pages.
Chinese Office Action for Application No. 201480015025.7, dated Jan. 23, 2018, 11 pages excluding English summary.
Chinese Office Action for Application No. 201480015036.5, dated Jan. 23, 2018, 13 pages excluding English translation.
European Office Action for Application No. 14779655.1, dated Mar. 8, 2018, 7 pages.
Japanese Office Action in Application No. 2016-501081, dated Feb. 9, 2018, 4 pages.
Memo concerning Mexican Office Action for Application No. MX/a/2015/015959, memo dated Mar. 2, 2018, 1 page.
Chinese Office Action for Application No. 201480015025.7, dated Oct. 9, 2018, 27 pages.
Chinese Office Action for Application No. 201480015036.5, dated Sep. 29, 2018, 20 pages.
Chinese Office Action for Application No. 201480041362.3, dated Oct. 18, 2018, 13 pages.
Japanese Office Action for Application No. 2016-501081, dated Nov. 2, 2018, 6 pages.
Canadian Office Action for Application No. 2828898, dated Dec. 7, 2018, 5 pages.
Australian Office Action for Application No. 2014241022, dated Sep. 30, 2019, 4 pages.
Chinese Office Action for Application No. 201480015036.5, dated Nov. 5, 2019, 12 pages.
Chinese Office Action for Application No. 201480041985.0, dated Sep. 23, 2019, 24 pages.
European Communication for Application No. 14779655.1, dated Oct. 2, 2019, 12 pages.
Japanese Office Action for Application No. 2016501081, dated Nov. 12, 2019, 6 pages.
India Office Action for Application No. 7050/CHENP/2013, dated Sep. 18, 2019, 7 pages.
Australian Office Action for Application No. 2014241019, dated Aug. 12, 2019, 4 pages.
Australian Office Action for Application No. 2014241022, dated Jun. 25, 2019, 3 pages.

(56) References Cited

OTHER PUBLICATIONS

Australian Office Action for Application No. 2018232958, dated Aug. 7, 2019, 3 pages.
Australian Decision Issued for Application No. 2014268828, dated Feb. 26, 2021, 30 pages.
Canadian Office Action for Application No. 2912792, dated Mar. 1, 2021, 7 pages.
Australian Office Action for Application No. 2020200812, dated Mar. 24, 2021, 5 pages.
Canadian Office Action for Application No. 2900564, dated Nov. 19, 2020, 4 pages.
Canadian Office Action for Application No. 2901024, dated Nov. 20, 2020, 6 oages.
Extended European Search Report for Application No. 20191537.8, dated Dec. 17, 2020, 9 pages.
Japanese Office Action for Application No. 2019-030891, dated Nov. 26, 2020, 5 pages including English translation.
Australia Office Action for Application No. 2014268828, dated Jul. 3, 2020, 5 pages.
Chinese Office Action for Application No. 201480041985.0, dated May 15, 2020, 23 pages.
India Office Action for Application No. 2625/KOLNP/2015, dated Jul. 8, 2020, 7 pages.
India Office Action for Application No. 4041/KOLNP/2015, dated Jul. 8, 2020, 8 pages.
Japanese Office Action for Application No. 2019-030891, dated May 27, 2020, 8 pages.
Australian Office Action for Application No. 2020201641, dated Oct. 9, 2020, 4 pages.
Canadian Office Action for Application No. 2551903, dated Aug. 18, 2020, 3 pages.
Canadian Office Action for Application No. 2828898, dated Oct. 7, 2020, 7 pages.
Chinese Office Action for Application No. 201480041985.0, dated Sep. 3, 2020, 38 pages.
Australian Office Action for Application No. 2014241019, dated Dec. 5, 2019, 5 pages.
Australian Office Action for Application No. 2014268828, dated Nov. 25, 2019, 3 pages.
Canadian Office Action for Application No. 2828898, dated Dec. 3, 2019, 6 pages.
Canadian Office Action for Application No. 2901024, dated Jan. 27, 2020, 5 pages.
Chinese Office Action for Application No. 201480015025.7, dated Nov. 12, 2019, 20 pages.
Chinese Office Action for Application No. 201480015093.3, dated Dec. 4, 2019, 17 pages.
European Office Action for Application No. 14801713.0, dated Dec. 11, 2019, 6 pages.
United Arab Emirates Office Action from KIPO for Application No. UAE/P/1554/2015, 11 pages.
Canada Office Action for Application No. 2900564, dated Jan. 28, 2020, 4 pages.
Brazil Office Action for Application No. BR112015029135-0, dated Feb. 12, 2020, 5 pages.
Brazil Office Action for Application No. BR112015019758-2, dated Feb. 20, 2020, 5 pages.
European Office Action for Application No. 14801726.2, dated Nov. 19, 2019, 7 pages.
Chinese Office Action for Application No. 201480041362.3, dated Aug. 5, 2019, 13 pages.
Australian Office Action for Application No. 2020203449, dated May 26, 2021, 5 pages.
Chinese Notice of Reexamination for Application No. 201480015036.5, dated Jul. 29, 2021, 32 pages including machine translation.
Chinese Office Action for Application No. 201480041985.0, dated Jun. 2, 2021, 4 pages including translation.
Canadian Office Action for Application No. 2828898, dated Aug. 25, 2021, 5 pages.
Canadian Office Action for Application No. 2901024, dated Aug. 25, 2021, 6 pages.
Chinese Notice of Reexamination for Application No. 201480015025.7, dated Aug. 20, 2021, 29 pages including translation.
European Office Action for Application No. 20191537.8, dated Aug. 18, 2021, 10 pages.
Japanese Office Action for Application No. 2019-030891, dated Aug. 24, 2021, 4 pages including translation.

* cited by examiner

MEDICATION WORKFLOW MANAGEMENT

BACKGROUND

Field

The present disclosure generally relates to medication distribution, and, in particular, relates to systems and methods for managing preparation, delivery, and recycling of a medication in a healthcare facility through harmonized integration of previously incompatible systems.

Description of the Related Art

A hospital pharmacy must manage and keep track of numerous medication orders to fit the needs of its patients. The various phases or steps of providing medication to patients are often carried out by various machines or personnel spread across various locations throughout the hospital.

In cases of patients admitted to a healthcare facility, one or more medications for a patient or infusions to be administered to the patient are prescribed by the patient's physician. A pharmacy, generally located within the patient's hospital or healthcare facility, prepares the medication according to the physician's prescription, for example, in a cleanroom (e.g., an environment having a controlled level of contamination that is specified by a number of particles per cubic meter at a specified particle size). In cases where the medication is an infusion solution, a compounder, such as a fully automatic or robotic compounder requiring minimal human operation, a partially-robotic or semi-robotic compounder requiring some human operation, or a manual compounder requiring a human operator, can be used to prepare the medication. After preparation, an appropriately trained and credentialed pharmacist places the infusion solution in a bag, bottle, syringe, or other container and labels the container.

The infusion solution is then staged in a pickup location, such as a bin-sorting area. A sorting person is then responsible for placing each prepared medication into bins or delivery carts that correspond to the locations where the medications will be delivered, such as an Intensive Care Unit (ICU). A delivery person retrieves the medications from the bins that correspond to areas of the healthcare facility to which that delivery person delivers. The delivery person then delivers the medications to the appropriate locations of the healthcare facility.

The medication is then delivered to the patient's location, and if the medication is an infusion solution, a clinician such as a nurse or other clinician hangs the infusion solution from a rack. The nurse connects a tube between the infusion solution and an infusion pumping system and inserts a cannula at the end of the tube into the vessel of the patient for delivery of the infusion solution to the patient.

SUMMARY

According to certain implementations of the present disclosure, a method of managing medications comprises interfacing with (i) a medication preparation component configured to fulfill a plurality of medication orders based on a first set of parameters, (ii) an inventory management component configured to stock an inventory based on a second set of parameters, (iii) a delivery management component configured to deliver medications based on a third set of parameters, and (iv) a medication recycling management component configured to retrieve unused medications based on a fourth set of parameters. The method further comprises providing the medication preparation component the first set of parameters based on the second, third, and fourth set of parameters, wherein the medication preparation component cannot interface directly with the second, third, and fourth set of parameters.

In another implementation of the present disclosure, a method of managing medications comprises receiving a plurality of medication orders for a plurality of medications, each of the plurality of medication orders having a preparation status, identifying an unused medication and a current location of the unused medication, identifying a component medication in an inventory, providing a preparation instruction to prepare a medication for at least one of the plurality of medication orders using the component medication when the at least one of the plurality of medication orders cannot be fulfilled by the unused medication, providing delivery instructions for delivering the medication based on the preparation status of each of the plurality of medication orders, and receiving a delivery verification of the medication.

In yet another implementation of the present disclosure, a non-transitory machine-readable medium contains machine-readable instructions for causing a processor to execute a method for managing medications. The method comprises receiving a plurality of medication orders for a plurality of medications, each of the plurality of medication orders having a preparation status, identifying an unused medication and a current location of the unused medication, identifying a component medication in an inventory, providing a preparation instruction to prepare a medication for at least one of the plurality of medication orders using the component medication when the at least one of the plurality of medication orders cannot be fulfilled by the unused medication, providing delivery instructions for delivering the medication based on the preparation status of each of the plurality of medication orders, and receiving a delivery verification of the medication.

At the various stages of medication preparation and delivery, verification of proper steps and/or procedures may be required. However, verification may be a complex procedure particularly when the various devices operate within proprietary parameters which may be incompatible with other devices in the workflow.

Examples of the various component systems and methods are described in U.S. patent application Ser. No. 13/901,501 entitled "Medication Preparation Queue," filed May 23, 2013, U.S. patent application Ser. No. 13/901,497, entitled "Component Based Aggregation of Medication Orders," filed May 23, 2013, U.S. patent application Ser. No. 13/900,482, entitled "Medication Delivery Management," filed May 22, 2013, U.S. patent application Ser. No. 13/900,502, entitled "Medication Retrieval Optimization," filed May 22, 2013, and U.S. patent application Ser. No. 13/900,493, entitled "Managing Re-Use of Returned Medications," filed May 22, 2013, the entire contents of which are incorporated by reference herein.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 3 illustrates an example process for managing preparation of a medication using the server of FIG. 2.

DETAILED DESCRIPTION

Figure 1:
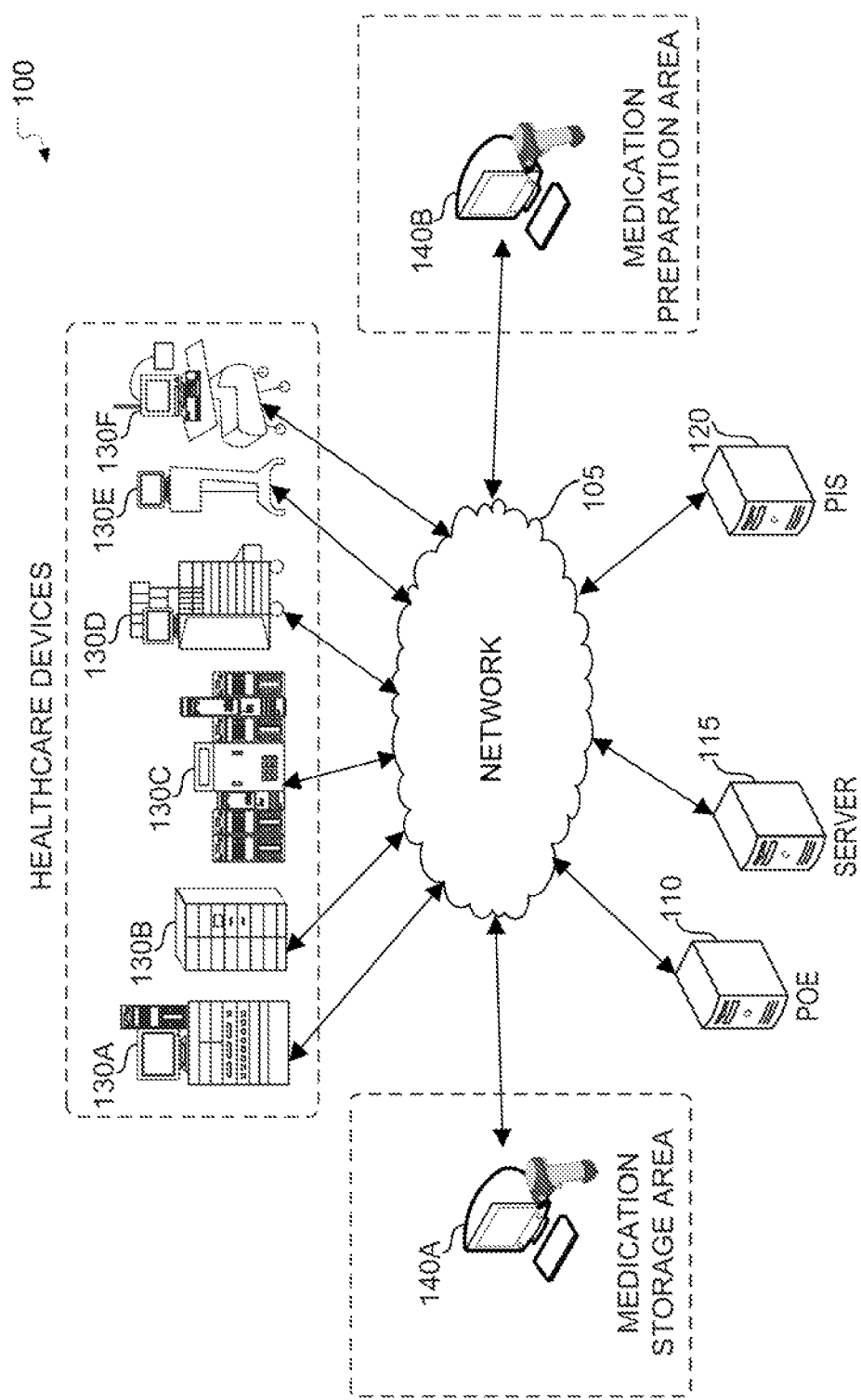
FIG. 1 illustrates an example hospital network environment in which a system for interfacing various devices may be implemented according to example aspects of the present disclosure.

In the following detailed description, numerous specific details are set forth to provide a full understanding of the present disclosure. It will be apparent, however, to one ordinarily skilled in the art that the embodiments of the present disclosure may be practiced without some of these specific details. In other instances, well-known structures and techniques have not been shown in detail so as not to obscure the disclosure.

The disclosed methods provide a process for managing the various devices and procedures throughout a medication workflow. For example, various components, such as a medication preparation component, and a delivery component, may operate independently of each other without being aware of each other. By providing an interface between the two, which my require reconciling incompatible data parameters, the workflow may be made more efficient. The interface may further reduce time necessary in actively managing the different data parameters, such as inconsistent identification (ID) parameters.

The interfacing of the various components provides for efficiency in the workflow. For instance, medication orders are taken from an electronic data feed such as a Health Level 7 (HL7) feed. Data from the feed is processed in order to identify various aspects of each order to add to the virtual queue. The system then determines whether the order for the medication can be filled with an already prepared medication item or a returned or retrievable unused medication item, or whether the order should be filled by preparing a medication item from components available in storage. Appropriate instructions for filling the order are provided for display in the queue based on how the order can be filled. In certain instances, a notification or preferred retrieval route may be provided to a delivery person to retrieve a medication item if the retrievable medication item can be used to fill the order.

The electronic data feed is monitored to update, in real-time, an order for a medication in the queue if, for example, a patient is discharged and the order for the patient is no longer needed. The queue will continually update based on changes from the electronic data feed. Thus, if an order is changed or discontinued, the entry for the order will be immediately updated in the queue. This will result in preventing a compound medication from being made that is no longer needed at that point in time, thereby preventing or reducing waste. This will also result in preventing or limiting dispensing of a product out for delivery or finalized and ready for delivery that may no longer be needed by a patient. This will further result in decreasing inefficient use of labor, and keeping a prepared medication on hand to potentially be used for a new order.

Each order for a medication is placed at a position in the virtual queue based on various factors including, for example, an estimated amount of time to prepare the medication, an estimated amount of time to deliver the medication to a delivery location, an estimated time at which the medication will be needed for administration to a patient at the delivery location, a delivery deadline for the medication, a degree of urgency for delivery of the medication, a type of the medication, or a component of the medication. Two or more medication orders that require the same or similar medication components may be grouped together in the queue, for example, to avoid unnecessary wasting of the component. The disclosed system is also configured to capture images or barcode readings of each component used to prepare the medication for the order, and the images or barcode readings may be provided to a local or remote pharmacist or other authorized inspector for verification that the medication for the order has been prepared with the appropriate components. Upon verification, the virtual queue is updated to reflect that the order has been filled and that the prepared medication for the order may be retrieved for delivery to a patient.

The disclosed system determines, upon a delivery person identifying (e.g., by scanning) a medication, such as an infusion solution, to be delivered, whether there are any other prepared or almost prepared medications that need to be delivered to the area of the hospital to which the delivery person is delivering the identified medication. If another medication is available or almost prepared for delivery, and it would be preferable to deliver the other medication during the same delivery as the identified medication, such as based on an urgency of the other medication or an expiration or delivery time of either medication, then a notification is provided to the delivery person to wait for the other medication to arrive for the appropriate bin prior to leaving to deliver the identified medication. The notification can be provided as an alert on a display of a device at or near the bin-sorting area, and/or may be sent to a device of the delivery person, such as the delivery person's mobile device. If another medication is available or almost prepared for delivery, but it is not preferable to deliver the other medication during the same delivery as the identified medication, then either no notification is provided to the delivery person, or a notification is provided to the delivery person to proceed with delivering the identified medication.

In this manner, the disclosed system provides the delivery person with insight into the medication preparation process by determining whether the delivery person should request (for delivery to the appropriate bin) a prepared medication that is sitting in the bin-sorting area from a sorting person, or whether the delivery person should wait for an medication to finish being prepared. The disclosed system may determine how urgently the medications identified (e.g., scanned) for delivery need to be delivered by the delivery person, and how long the delivery person will need to wait to obtain any other medication for which the preparation is almost complete. The disclosed system may notify (e.g., by a visible or audible alert, such as a text message or notification window) the delivery person of an medication that is almost prepared if the system determines that the delivery person has sufficient time to wait for the preparation of the medication to complete, (e.g., based on an estimated amount of time required to complete the preparation of the medication), the times that the identified medications need to be delivered by, and an estimated amount of time required to deliver the identified medications.

In addition, the disclosed system provides a delivery person who is delivering infusion solutions to a particular area of a healthcare facility with a list of discontinued infusion solutions and their location in the area to which the delivery person is delivering. The delivery person may then retrieve the discontinued infusion solutions and return them to a pharmacy location providing services within a facility. The discontinued infusion solutions may be scanned upon their return to the pharmacy and listed in an inventory of available infusion solutions. In certain aspects, the discontinued infusion solutions may be scanned when initially retrieved by the delivery person and also be listed in the inventory of available solutions. If the discontinued infusion solutions have passed their expiration date, or are not within a threshold time duration of their expiration date, (e.g., exceeding the amount of time required to deliver to and administer the infusion solution at another location), then the discontinued infusion solutions are discarded. However, if the discontinued infusion solutions are not within the threshold time duration of their expiration date, the discontinued infusion solutions are re-entered into inventory for possible re-use. In certain aspects, the expiration date of an infusion solution can be automatically determined based on the stability and sterility of the medication.

When a new order for an infusion solution is received, the disclosed system first checks whether the discontinued infusion solution that has been re-entered into inventory can be used to fill the new order. If the order can be filled with the discontinued infusion solution, then the discontinued infusion solution is used for the order. However, if the order cannot be filled with the discontinued infusion solution, then the order is placed in an infusion solution preparation queue for preparation by a technician or pharmacist.

In certain aspects, the disclosed system may determine one or more metrics regarding the number of discontinued infusion solutions that are re-entered into inventory and/or the number of discontinued infusion solutions that are discarded. The disclosed system may, for example, utilize the one or more metrics to adjust a suggested number of infusion solutions that are prepared without any corresponding orders on a daily basis, (e.g., the number of fast mover pre-pack infusion solutions that are prepared on a daily basis). For example, if a large number of discontinued orders for a particular fast mover pre-pack infusion solution is being re-entered into inventory on a daily basis, and the fast mover pre-pack infusion solutions subsequently expire before they can be administered to a patient, the disclosed system may reduce the suggested number of the fast mover pre-packs that should be prepared on a daily basis.

FIG. 1 illustrates an example hospital network environment 100 in which a system for managing a medication workflow may be implemented in accordance with example aspects of the present disclosure. Not all of the depicted components may be required, however, and one or more implementations may include additional components not shown in FIG. 1. Variations in the arrangement and type of the components may be made without departing from the spirit or scope of the claims as set forth herein. Additional, different or fewer components may be provided.

The example hospital network environment 100 includes a network 105, a physician order entry (POE) system 110, a server 115, a pharmacy information system (PIS) 120, one or more healthcare devices 130A-F, an electronic device 140A that is located in a medication storage area, and an electronic device 140B that is located in a medication preparation area. In one or more implementations, the medication storage area may be an area where a medication inventory of a healthcare facility is stored, and the medication preparation area may be an IV workroom or compounding station, such as a clean workroom, a sterile workroom, and/or a non-sterile workroom. Other types of medication storage areas and/or medication preparation areas are also possible, such as nurse stations.

The POE system 110, PIS 120, healthcare devices 130A-F, and/or electronic devices 140A-B may be communicatively coupled to one another, such as by the network 105. In one or more embodiments, one or more of the POE system 110, the PIS 120, the healthcare devices 130A-F, or the electronic devices 140A-B may be directly coupled to one another. In addition, there may be a number of other devices connected to the network 105, such as a control system, additional healthcare systems, (e.g., a hospital information system (HIS), a laboratory information system (LIS), or other clinical and/or logistical systems), additional healthcare devices, additional electronic devices, external systems, computing devices, mobile devices, etc. The POE system 110, the PIS 120, one or more of the healthcare devices 130A-F, and/or one or more of the electronic devices 140A-B may be, or may include all or part of, the electronic system that is discussed further below with respect to FIG. 5.

The network 105 may be a communication network, such as a public communication network (such as the Internet, cellular data network, dialup modems over a telephone network), a private communications network (such as private local area network ("LAN"), leased lines), etc. The network 105 may also include, but is not limited to, any one or more of the following network topologies, including a bus network, a star network, a ring network, a mesh network, a star-bus network, a tree or hierarchical network, and the like. The connections of the network 105 may be wired or wireless. For example, one or more of the POE system 110, the server 115, the PIS 120, the healthcare devices 130A-F, and/or the electronic devices 140A-B may transmit wireless signals over the network 105, such as wireless Ethernet signals, radio frequency (RF) signals, infrared (IR) signals, Bluetooth signals, or any other means capable of carrying information in a wireless manner between devices having appropriate transmitters and/or receivers.

The POE system 110, the server 115, and/or the PIS 120 may be single computing devices, such as computer servers. Alternatively, the POE system 110, the server 115 and/or the PIS 120 may represent one or more computing devices (such as a cloud of computers and/or a distributed system) that are communicatively coupled, such as communicatively coupled over the network 105, and that collectively, or individually, perform one or more functions that can be performed server-side, such as receiving messages, transmitting messages, storing messaging, receiving control commands, providing user interfaces, transmitting notifications, etc. The POE system 110, the server 115, and/or the PIS 120 may be coupled with various databases, such as data stores, storage services, or other computing devices.

The server 115 may be a system or interface engine configured to interface with the other devices, including the POE system 110, the PIS 120, the healthcare devices 130A-F, and/or the electronic devices 140A-B (collectively referred to as the other devices). For example, the server 115 may be able to interface with each of the other devices and further provide an interface between each of the other devices even if normally one or more of the other devices are incompatible, or otherwise operate on unique or proprietary parameters. The server 115 may provide feedback on the operation of one or more of the other devices, and may further automate the medication workflow by providing instructions to one of more of the other devices based on feedback. The server 115 may act as an interface engine which reconciles the various systems of the other devices without requiring real-time mapping across multiple systems. The server 115 may also be configured to support additional devices such that the addition of one or more devices provides seamless integration with the other devices already in use.

The POE system 110, the server 115, and/or the PIS 120 may be systems that facilitate with providing healthcare, and/or provide healthcare. The POE system 110 may be used, for example, by physicians to enter orders for patients, such as orders for medications to be administered to patients. The orders for medications may be transmitted to the PIS 120 for preparation. The PIS 120 may store, for example, information pertaining to a pharmacy of a healthcare facility, such as outstanding orders, filled orders, medication inventory, patient medical profiles/histories, etc. For example, the PIS 120 may be coupled to a database that stores, for example, an inventory of the medications that are stored in the medication storage area and/or medications that are temporarily stored in one or more medication preparation areas.

The healthcare devices 130A-F may include infusion devices, such as infusion pumps, drug delivery devices, dispensing devices, such as automated dispensing machines, monitoring devices, respiratory devices, such as ventilators, waste devices, such as drug disposal devices, or generally any device that may facilitate with providing healthcare and/or may provide healthcare. One or more of the healthcare devices 130A-F may include a processor and/or a memory. Alternatively, or in addition, one or more of the healthcare devices 130A-F may be communicatively coupled to a device that includes a processor and a memory, such as via a serial port.

For example, the healthcare devices 130A-F may include automated dispensing machines (ADM), such as Pyxis Medstations™, which store and dispense medications at nurse's stations, thereby providing distributed access to medications. The healthcare devices 130A-F may further include infusion devices, such as infusion pumps, that assist with administering medications to patients. The healthcare devices 130A-F may also include waste devices that accept and store wasted medications, for example, excess medications, from healthcare professionals and track the amount of medications wasted by healthcare professionals. One or more of the healthcare devices 130A-F that provide medications, (e.g., that provide access to medications or that administer medications), may transmit signals, such as replenishment signals, to the PIS 120 when the medications need to be replenished. For example, an intravenous (IV) pump may transmit a replenishment signal when an IV bag that is being administered to a patient needs to be replenished. Similarly, an automated dispensing machine may transmit a replenishment signal when one or more of the medications distributed by the automated dispensing machine are running low. The server 115 may facilitate the transmission of these signals to the appropriate device in the appropriate format.

The electronic devices 140A-B may be any electronic devices such as laptop or desktop computers, mobile phones, personal digital assistants ("PDAs"), tablet computers, televisions or other displays, or other appropriate computing devices that can be used to display user interfaces that facilitate with, for example, picking component medications for ordered medications and/or preparing ordered medications. For instance, the electronic device 140A that is located in the medication storage area may display a queue to facilitate with retrieving, or picking, medications from inventory for received orders in a manner that substantially minimizes waste, while the electronic device MOB that is located in the medication preparation area may display a queue to facilitate with preparing ordered medications in a manner that substantially minimizes waste.

In the example of FIG. 1, the electronic devices 140A-B are depicted as desktop computers; however, the electronic devices 140A-B may be any of the aforementioned electronic devices, and/or any other electronic devices. For example, the electronic device 140B may be a compounder or other device including hardware or machinery to physically perform one or more steps of medication preparation. The electronic devices 140A-B may include a processor and/or a memory. The electronic devices 140A-B may include input devices that may be used to select or identify component medications and/or containers that contain component medications, for instance, by scanning a label attached to a container. The input devices may include, for example, bar code scanners, radio frequency identification (RFID) readers, or generally any devices that can recognize or identify a component medication, a container that contains a component medication, and/or a container that will be used to store an ordered medication.

For explanatory purposes, the electronic device 140A is described herein as being located in a medication storage area and the electronic device 140B is described herein as being located in a medication preparation area; however, the electronic devices 140A-B may be portable devices, (e.g., a tablet device or a mobile phone), that a healthcare professional may carry in and out of the medication storage area and/or the medication preparation area. The medication storage area and/or the medication preparation area may be located within a pharmacy of a healthcare facility. Alternatively, or in addition, the medication storage area and the medication preparation area may be disparately located within, or outside of, the healthcare facility. In one or more implementations, the healthcare facility may include multiple medication storage areas, one or more of which may include the electronic device 140A, and/or multiple medication preparation areas, one or more of which may include the electronic device 140B.

In operation, one or more orders for medications may be received by the PIS 120, such as from the POE system 110, or from one of the healthcare devices 130A-F, for example, in the form of a replenishment signal. An order may indicate at least one component medication, such as cefazolin, vancomycin, norepinephrine, saline solution, etc., along with an amount of the component medication to be used to prepare the medications. In one or more embodiments, the orders for medications may include orders for IV bags. The PIS 120 may transmit the orders to the electronic device 140A that is located in the medication storage area, such that the component medications of the orders can be picked or retrieved from the medication storage area by a healthcare professional, for instance. The server 115 may help facilitate the transmission of the orders and other related data.

In one or more embodiments, the healthcare facility may utilize anticipatory batching for fast moving compounds or components. For example, a determined amount of a medication that includes a particular compound or component may be prepared as an anticipatory batch, irrespective of whether any orders have been received for the medication. The anticipatory batch of the medication may be associated with one or more periodic automatic replenishment (PAR) levels. If the prepared amount of the medication from the anticipatory batch falls below a PAR level, a system, such as the PIS 120 or the server 115, may generate one or more orders for the medication, (e.g., an "auto-reorder"), based on the PAR levels set, and the one or more orders may be provided to the PIS 120 along with orders received from the POE 110 and/or from one or more of the healthcare devices 130A-F.

The electronic device 140A that is located in the medication storage area may aggregate the received orders into batches, or groups, based on the component medications that are indicated by each order. For instance, the electronic device 140A may batch the orders such that orders that have a common (e.g., the same) component medication are picked together. After batching the orders, for example based on the component medications, the electronic device 140A may select the first batch of orders and determine the containers from inventory that should be picked to prepare the first batch of orders in a manner that minimizes wasted component medications. The containers may include vials, bags, bottles, packages, or generally any container that can store a component medication. In one or more embodiments, the steps of batching the orders and determining the containers to be retrieved from inventory to prepare a batch of orders may be performed by the PIS 120, and/or another server system. The PIS 120 may then transmit the batches, along with the amount of component medications to be retrieved for each batch and/or the containers to be retrieved from inventory for each batch, to the electronic device 140A.

The electronic device 140A may determine a first batch of orders and may provide an indication of the component medications needed to prepare the first batch, the amount of the component medications that needs to be retrieved for the first batch, and the containers from inventory that should be retrieved for the first batch. For example, the electronic device 140A may display a user interface to facilitate the healthcare professional with picking the component medications for the first batch. The healthcare professional may retrieve the containers from the inventory of the medication storage area for preparing the first batch. For example, the healthcare professional may identify each container that is retrieved from inventory, for instance by scanning the containers with a bar code scanner. The electronic device 140A may transmit indications of the scanned containers to the PIS 120 and the PIS 120 may store an indication that the containers are being removed from the inventory of the medication storage area and being delivered to a temporary inventory of a medication preparation area. The server 115 may be an intermediary to facilitate the transmittal of identifiers, such that any proprietary or otherwise incompatible identifying system of any of the devices becomes compatible with the PIS 120 and other devices. The containers may then be delivered to the medication preparation area for preparation of the first batch of orders.

Once the containers containing the component medications for the first batch of orders are delivered to the medication preparation area, the electronic device 140B (that is located in the medication preparation area) receives an indication of the first batch of orders. The electronic device MOB may display, for example, to a healthcare professional who will be preparing the first batch of orders, a user interface that includes a queue that lists the first batch of orders. In one or more implementations, the electronic device 140B may order the queue such that the orders that will be prepared with a common component medication are displayed adjacently in the queue.

The electronic device 140B may receive an indication that the healthcare professional has initiated preparation of an order listed in the queue, and/or that the healthcare professional has selected an order listed in the queue. Upon receiving the indication, the electronic device 140B determines whether there are any other orders listed in the queue that will be prepared using the component medication of the order that is currently being prepared. If the electronic device 140B determines that any such orders are listed in the queue, the electronic device 140B may notify the healthcare professional of the orders and/or the electronic device 140B may re-order the queue, if necessary, such that the orders are listed in the queue adjacent to the order currently being prepared. In this manner, orders that are prepared using the same component medication can be prepared together, thereby minimizing any excess amount of component medication that is wasted.

Figure 2:
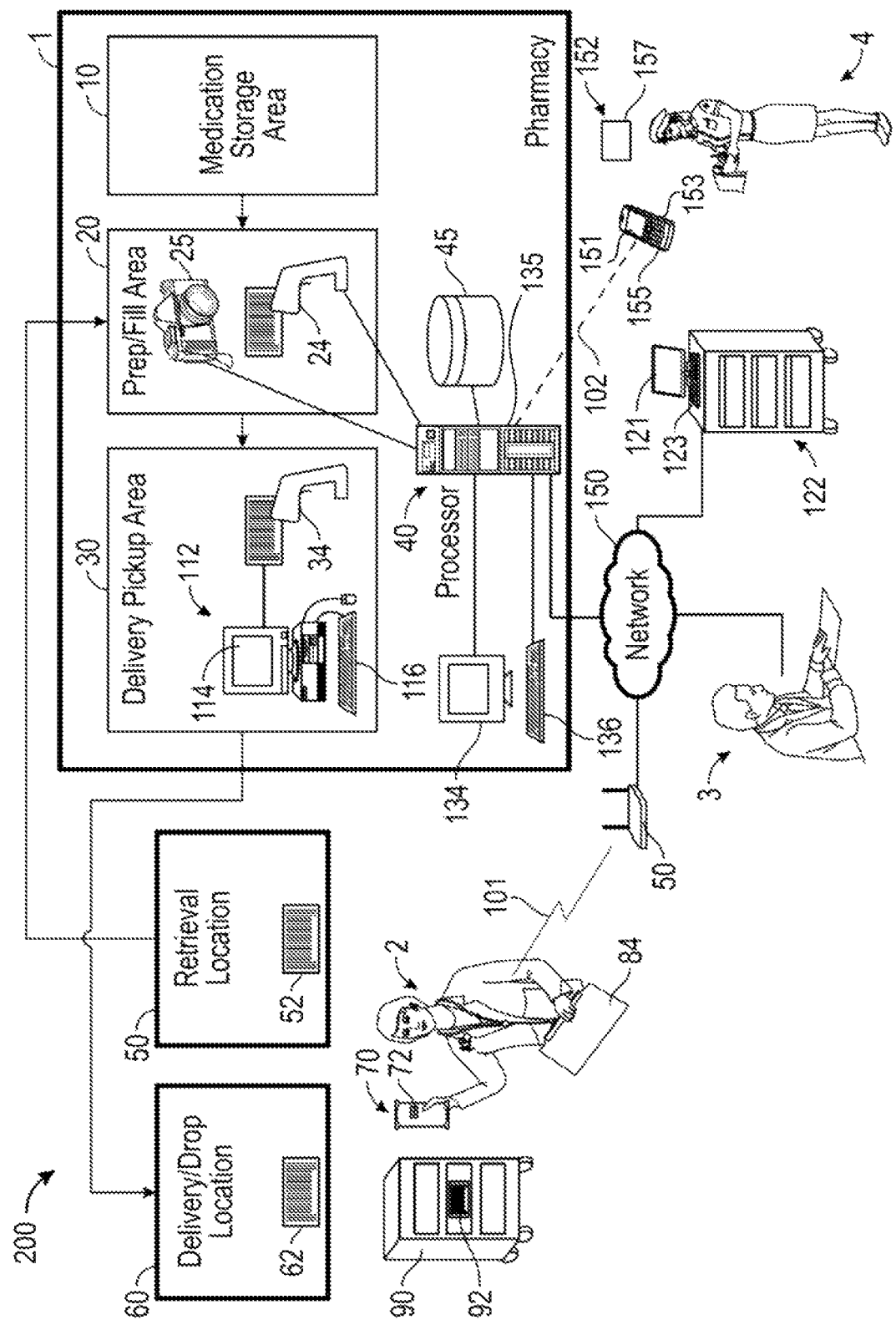
FIG. 2 illustrates an example architecture for managing preparation of a medication according to example aspects of the present disclosure.

Turning now to the drawings, FIG. 2 illustrates an example architecture 200 for managing preparation of a medication according to certain aspects of the present disclosure. For ease and clarity of illustration only, without any intent to limit the scope of the present disclosure any way, it is assumed that the prepared medication provided as an example for FIG. 2 is an anesthetic IV solution.

The architecture 100 includes a pharmacy 1 having a medication storage area 10, a fill and/or preparation (fill/prep) area 20, and a delivery pickup area 30 (e.g., bin-sorting area). The medication storage area 10 includes a plurality of medications and supplies including, for example, an anesthetic drug (e.g., bupivacaine or chloroprocaine) and an appropriate fluid for the anesthetic drug. The anesthetic drug and the fluid are taken from the medication storage area 10 to the prep/fill area 20 where they are mixed together to produce the anesthetic IV solution. A patient/medication ID device 72, such as a barcode label or a radio frequency identification (RFID) tag, is provided on (e.g., affixed to) a package 70 (e.g., IV bag) containing the IV solution at the prep/fill area 20. The patient/medication ID device 72 includes patient/medication ID information indicative of the medication and the patient to whom the medication is prescribed. The package 70 is then taken by a technician at the pharmacy 1 to the delivery pickup area 30. The technician determines an appropriate bin or delivery cart 90 into which to place the package 70, and then loads the package 70 onto the appropriate delivery cart 90 for delivery to a scheduled delivery/drop location 60 (e.g., a patient room) by a delivery person 2 (e.g., a person assigned the task of delivering medications, or a machine such as a robot configured to perform such task).

In the illustrated implementation, the prep/fill area 20 has a barcode reader 24 provided therein that the technician at the pharmacy 1 can use to read the patient/medication ID device 72 (a barcode label in the illustrated example) before the package 70 is taken to the delivery pickup area 30. The prep/fill area 20 may also have an image recording device 25, such as a camera, for recording preparation of the package 70. The delivery pickup area 30 has a barcode reader 34 connected to a client 112 provided therein that the technician at the pharmacy 1 can use to read the patient/medication ID device 72 once the package 70 is taken to the delivery pickup area 30. The delivery cart 90 may also be provided with a location barcode label reader. The delivery person 2 can use the barcode reader 34 to scan the package 70 to indicate the delivery person 2 will begin delivery of the package 70. A notification of delivery may be sent to a server 135.

The pharmacy 1 includes the server 135 (e.g., pharmacy server) that may correspond to (e.g., perform one or more functions of) the server 115, and includes a processor 40. The server 135 is coupled to an output device 134, such as a display, and an input device 136, such as a keyboard. The server 135 can be any device having an appropriate processor, memory, and communications capability for running a preparation tracking application and receiving, processing, and sending information associated with a medication database 45 and prepared medications. The processor 40 is coupled to the medication database 45 that is configured to store a variety of information. The medication database 45 can include information such as, but not limited to: the patient's name or ID, the medication name or ID, the scheduled delivery location 60, the scheduled delivery time, an expiration date or time for a prepared medication, an estimated administration time for the prepared medication, an urgency of delivery of the prepared medication, a current location of the prepared medication, an order status of the prepared medication, a return status of the prepared medication, one or more read locations where the medication/patient ID information and/or the location ID information was read by a barcode scanner 84, a time when the information was read, and the name or ID of the delivery person 2. The medication database 45 is configured to electronically provide and receive the information according to various interoperability standards or parameters, such as the HL7 standard, which can include data received from various medical devices such as an infusion pump. The electronic data feed providing the HL7 standardized data is different than a printer feed in which data is not provided for exchange, integration, sharing, and retrieval of electronic health information as with the HL7 standardized data. For example, the electronic data feed can include data formatted for the HL7 standard that indicates a current or past status of an infusion pump, respiratory device, dispensing machine, or other medical device. However, certain devices or machines, such as compounders or other devices in the prep/fill area 20, may not be compatible with or able to directly interface with the interoperability standards or parameters, due to, for example, being configured for a proprietary or custom-built data parameters. The processor 40 may reconcile the incompatibilities between various data standards or parameters. For example, before or while storing data in the database 45, the processor 40 may convert, using a look-up table, a hash table, or other appropriate algorithm, non-standard data into standardized data. Alternatively, the database 45 may store the non-standardized data, and may convert the data before or during its retrieval.

The processor 40 of the server 135 at the pharmacy 1 is configured to electronically receive information or data from the medication database 45 according to an interoperable standard such as the HL7 standard and process the information to identify one or many orders to be prepared in the prep/fill area 20 of the pharmacy L In certain implementations, one or more devices may require data in a non-standard format or parameters. The processor 40 may either receive data and convert into a compatible parameter or format, or alternatively may specifically request and receive non-standard data from the database 45. The processor 40 then determines whether each order can be filled using an available medication that has already been prepared (e.g., in the medication storage area 10), a retrieved or retrievable medication that will no longer be needed by another patient, or whether the order must be filled by preparing a new medication. As such, the processor 40 is configured to make the determinations in "real-time," namely, substantially immediately in response to corresponding data from the medication database 45. In addition, the start or completion of the various tasks described herein may send a corresponding notification or verification to the server 135, through being scanned, for instance.

A medication order may be prepared by a physician 3 (e.g., a doctor, other authorized personnel, or machine such as a robot assigned the task of determining prescriptions for patients). The physician 3 may send medication orders through a POE (not shown in FIG. 2) or other device.

A medication may be retrieved by the delivery person 2 and returned to the pharmacy 1. The retrieved medication may be scanned upon its return to the pharmacy 1 and listed in an inventory of available retrieved medications. In certain aspects, the retrieved medication may be scanned when initially retrieved (e.g., but not yet returned to the pharmacy 1) by the delivery person 2 and also be listed in the inventory of available solutions. If the retrieved medication has passed its expiration date, or is not within a threshold time duration of its expiration date, (e.g., exceeding the amount of time required to deliver to and administer the retrieved medication at another location), then the retrieved medication is discarded. However, if the retrieved medication is not within the threshold time duration of its expiration date, the retrieved medication is re-entered into inventory for possible re-use.

The processor 40 of the server 135 at the pharmacy 1 provides appropriate notifications to an output device 134 based on the determination whether each order can be filled using an available medication that has already been prepared, a retrieved or retrievable medication that will no longer be needed by another patient, or whether the order must be filled by preparing a new medication, including, for example, how the order should be filled, and a location of a retrievable medication that can be used to fill the order. For example, a notification can be displayed on the output device 134 indicating that a retrieved medication for bupivacaine IV solution and be used to fill a new order for bupivacaine IV solution. In determining whether retrieved or retrievable medication can be used to fill the order, the processor 40 is configured to calculate the expiration date of the retrieved or retrievable medication. The expiration date of the retrieved or retrievable medication is used to determine whether the retrieved or retrievable medication can be used to fill the order.

The processor 40 is configured to determine an expiration date for a returned package 70 based on, for example, the stability and sterility of the returned package 70. Information indicative of the stability and sterility of the returned package 70 may be obtained from the medication database 45. For example, the stability of the returned package 70, which indicates a length of time a drug in the returned package 70 retains its properties without loss of potency (i.e., "shelf life") can initially be entered by a pharmacist or other health care provider when the returned package 70 is first prepared. The sterility of the returned package, which indicates the conditions in which the package 70 was prepared (e.g., an environment particle count), can be determined based on a known location in which the package 70 was prepared as stored in the medication database 45. For instance, if the package returned package 70 is prepared in a sterile zone, it may be given a longer expiration time frame than if the returned package 70 were not prepared in a sterile zone. The processor 40, based on a stability date entered by a pharmacist and a sterility indicator calculated based on the known location in which the package 70 was prepared, can then generate an expiration date for the returned package 70.

In certain aspects where a retrieved or retrievable medication can be used to fill the order, an identification of the retrievable medication and of the retrieval location 50 can be provided to a client 112 in or associated with the delivery pickup area 30 for display on an output device 114 at or near the delivery pickup area 30 instructing the delivery person 2 to retrieve the retrievable medication from the retrieval location 50. A route for retrieving the retrievable medication from the retrieval location 50 (e.g., a patient room) may also be provided to the client 112 based on, for example, current deliveries being made by the delivery person 2. The client 112 can be, for example, a computer system associated with the delivery pickup area 30 such as a desktop computer or mobile computer. The client 112 can also be, for example, a tablet computer, mobile device (e.g., a smartphone or PDA), or any other device having appropriate processor, memory, and communications capabilities. A client 112 that is a mobile device may, for example, be associated with the delivery person 2.

Upon determining how the order from the medication database 45 can be filled, the processor 40 of the server 135 in the pharmacy 1 provides an entry for the order for display on the output device 134 of the server 135 and in a virtual queue of orders to be filled by the pharmacy 1. The entry for the order is listed at an appropriate position in the queue among any other order(s) in the queue. The position of each order for a medication in the queue as determined by the processor 40 may be based on, for example, an estimated amount of time to prepare the medication, an estimated amount of time to deliver the medication to the delivery/drop location 60, an estimated time at which the medication will be needed for administration to a patient at the delivery/drop location 60, a delivery deadline for the medication, a degree of urgency for delivery of the medication, a type of the medication, or a component of the medication. Two or more medication orders that require the same or similar medication components may be grouped together in the queue, for example, to avoid unnecessary wasting of the component used to prepare the medication.

Records of the preparation of the medication for the order using one or more components is recorded and stored in the medication database 45 for later verification by a pharmacist or other inspector responsible for authorizing the prepared medication as being ready for delivery to a patient. The records can include, for example, images or video recorded by the image recording device 25 or barcodes for the component(s) read by the barcode reader 24. The records may then be provided to the pharmacist for verification. Upon verification, the package 70 prepared for the order is identified as prepared in the queue and ready for delivery to the delivery/drop location 60 by the delivery person 2. At any time, if the medication database 45 indicates that the order has changed, such as due to a status change of the patient for whom the order is written, the queue is automatically updated to modify or remove the listing for the order in the queue based on the change to the order indicated by the medication database 45.

The delivery location 60 and/or the retrieval location 50 can include, for example, patient rooms having an infusion device for providing an IV infusion from a package to a patient. In the illustrated example, the retrieval location 50 and the delivery location 60 are provided with location barcode label 52 and location barcode label 62, respectively. Each of the location barcode labels 52, 62 includes unique location ID information indicative of the respective location 50, 60 where the corresponding barcode label is provided. As described above, the package 70 (e.g., IV bag) containing the medication (e.g., IV solution) is provided with a patient/medication identification (ID) device 72. In the illustrated example, the patient/medication ID device 72 is a barcode label that includes patient/medication information indicative of the patient (e.g., "Jane Smith") and the medication (e.g., "bupivacaine IV solution"). The patient/medication information may also contain other drug or patient related information such as the patient's medical conditions (e.g., allergies), name of the drug (e.g., bupivacaine), the drug dosage, the drug concentration, the drug administration schedules, and the drug administration rate.

Also depicted in the architecture 200 of FIG. 2 is a reader device 84 that is hand carried by the delivery person 2 and/or attached to the delivery cart 90 and is configured to read the patient/medication information from the patient/medication ID device 72 provided on the package 70. In the illustrated example, the reader device 84 is a barcode scanner. In those implementations in which the barcode scanner 84 is hand carried by the delivery person 2, the scanner 84 is also configured to read the location ID information from location barcode labels 52, 62, 92.

The location ID devices 52, 62, 92 and/or the patient/medication ID device 72 may be passive ID devices, meaning that certain action (e.g., scanning) has to be taken by the participant (e.g., a pharmacy technician or the delivery person 2) to retrieve information therefrom. In other implementations, the ID devices can be active ID devices, such as an active tracking device 157, meaning that the information retrieval from the ID devices occur automatically without an action taken by the participant. In some implementations, the active ID devices can actively transmit signals containing the relevant information to the reader device 72 through a wireless link. The wireless link can use a variety of technologies including Bluetooth, ZigBee, wireless USB, and proprietary systems. In other implementations, the active ID devices do not themselves transmit signals, but respond to query signals generated by a reader device (e.g., by altering impedance of an RF circuit therein) as the reader device passes by the ID devices in close proximity.

In the illustrated example, each time the barcode scanner 84 scans an ID device (e.g., patient/medication ID device or location ID device), the information read thereby is provided to the medication database 45 via wireless transmission 101 to a wireless bridge 50 that receives the information. The bridge 50 is in data communication with the processor 40 via a hospital network 150. The network 150 can include, for example, any one or more of a personal area network (PAN), a local area network (LAN), a campus area network (CAN), a metropolitan area network (MAN), a wide area network (WAN), a broadband network (BBN), the Internet, and the like. Further, the network 150 can include, but is not limited to, any one or more of the following network topologies, including a bus network, a star network, a ring network, a mesh network, a star-bus network, tree or hierarchical network, and the like. The network 150 may correspond to the network 105 in FIG. 1.

The processor 40 is configured to receive medication/patient ID information and/or location ID information read by the barcode scanner 84, generate location, use, and re-use information therefrom. The processor 40 is configured to store the information in the medication database 45.

The architecture 100 further comprises tracking devices 122, 152 that allow a care provider 4 (e.g., a nurse assigned the task of administering the patient-specific medication to the patient, or a machine such as a robot configured to perform such tasks) to monitor the progress of the delivery of the medication. Each of the tracking devices 122, 152 is configured to receive a tracking request by the care provider 4, access the medication database 45, either directly or via the processor 40, retrieve the delivery progress information stored in the database 45, and indicate a delivery progress of the medication to the care provider 4 based on the delivery progress information. In the illustrated example, the tracking device 122 is an automated dispensing machine having a processor (not shown), a display 121, and a keyboard 123; and the tracking device 152 is a mobile communication device 155 (e.g., a cell phone, personal digital assistant (PDA), or pager) having a processor (not shown), a display 151, and a keyboard 153, and may be connected to the server 135 through a wireless connection 102. The delivery progress information can inform the care provider 4 of a last-known read location and time of the last reading. Based on such information, the care provider 4 can decide, for example, whether to wait for the delivery at the delivery location 60, go to the delivery location later at an expected delivery time, or go to the last-known location to retrieve the medication from the cart 90.

Figure 3:
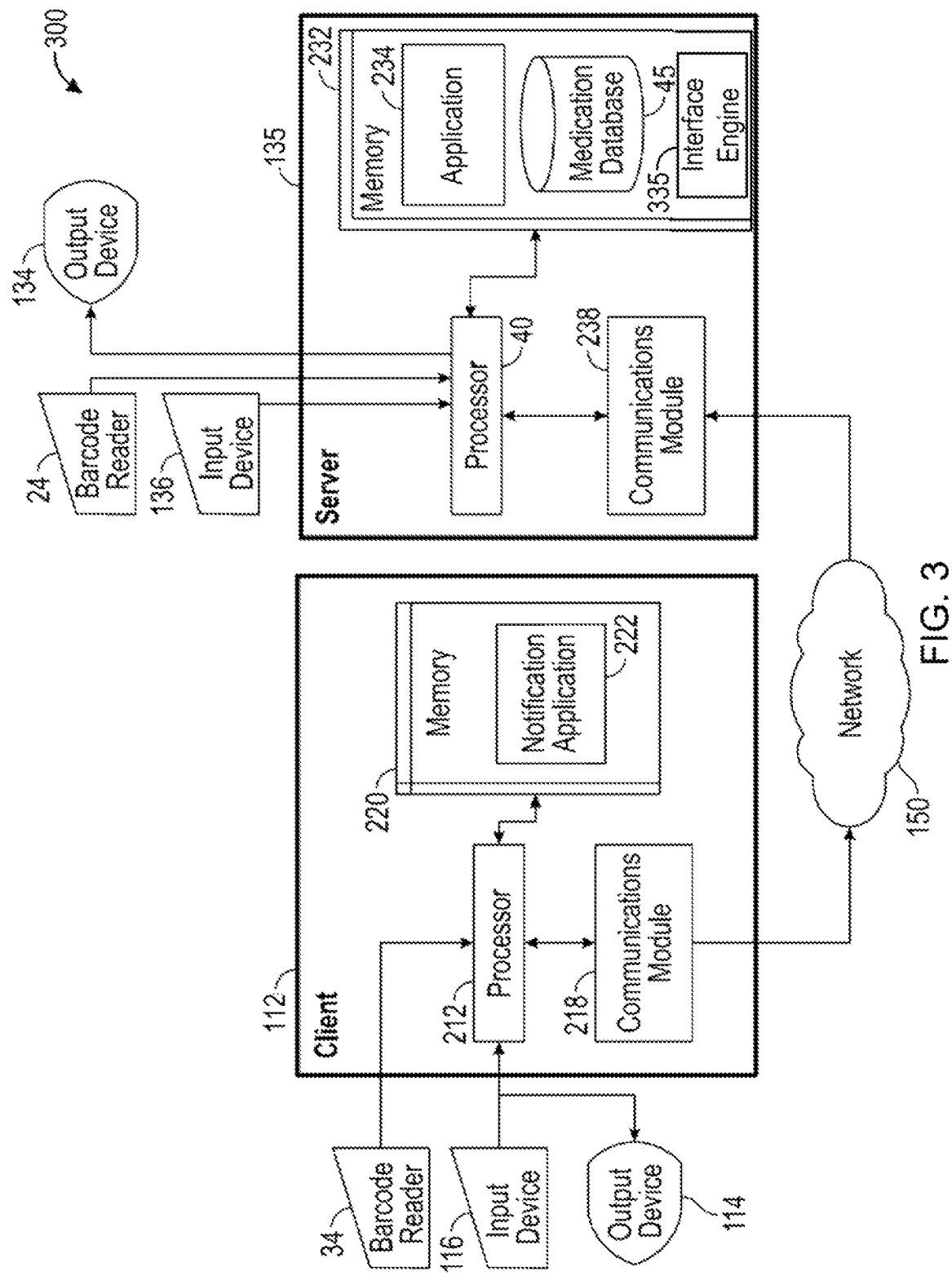
FIG. 3 is a block diagram illustrating an example client and server from the architecture of FIG. 2 according to example aspects of the disclosure.

FIG. 3 is a block diagram 300 illustrating an example server 135 and client 112 in the architecture 200 of FIG. 2 according to certain aspects of the disclosure. The client 112 and the server 135 are connected over the network 150 via respective communications modules 218 and 238. The communications modules 218 and 238 are configured to interface with the network 150 to send and receive information, such as data, requests, responses, and commands to other devices on the network 150. The communications modules 218 and 238 can be, for example, modems or Ethernet cards.

The client 112 includes a processor 212, the communications module 218, and a memory 220 that includes a notification application 222. The client 112 is further connected to the barcode reader 34, the input device 116, and the output device 114.

The server 135 includes a processor 40, a communications module 238, and a memory 232 that includes the medication database 45, an application 234, and an interface engine 335. The processor 40 of the server 135 is configured to execute instructions, such as instructions physically coded into the processor 40, instructions received from software in memory 232, or a combination of both. For example, the processor 40 of the server 135 executes instructions from the application 234 to receive information indicative of an order for medication for a patient from an electronic data feed (e.g., medication database 45) and determine whether the order can be filled with an available prepared medication or a returned medication.

A determination whether an available prepared or returned medication can be used to fill the order can be based on, for example, a comparison between at least two of an expiration time of the available prepared or returned medication, an estimated amount of time for delivering the available prepared or returned medication to the delivery/drop location 60, an estimated time at which the available prepared or returned medication will be administered to a patient at the delivery/drop location 60, and a delivery deadline for the available prepared or returned medication.

For example, if a returned medication is estimated to expire in ten minutes, and it is estimated to take thirty minutes to deliver the returned medication to the delivery/drop location 60, then the determination may indicate that the returned medication cannot be used for completing the order of the other medication. As another example, if the order must be delivered to the delivery/drop location 60 within two hours, and the estimated time to deliver an available prepared medication to the delivery/drop location 60 is one hour, then the determination may indicate that the available prepared medication should be used for completing the order. As yet another example, if a returned medication is estimated to expire in one hour, it is estimated to take thirty minutes to deliver the returned medication to the delivery/drop location 60, and the order must be delivered to the delivery/drop location 60 within forty-five minutes, then the determination may indicate that the returned medication can be used for completing the order of the other medication.

When the processor 40 determines the order can be filled with an available prepared medication or a returned medication, the processor 40 is configured to provide a notification to fill the order with the available prepared medication or returned medication. The notification can include, for example, an instruction to assist with preparation of the order using the prepared or returned medication. For instance, the notification can indicate that a returned medication should be combined with another returned medication to fill the order, and further indicate a pickup location (e.g., retrieval location 50) at which the medication can be retrieved if it is not yet retrieved. As an example, if two returned medications are each for Cefazolin (2 gm/NS 50 ml), and a new order for Cefazolin (4 gm/NS 100 ml) is received by the processor 40, then the processor 40 can send a notification (e.g., to output device 134) indicating that the two returned medications of Cefazolin (2 gm/NS 50 ml) should be combined to fill the new order for Cefazolin (4 gm/NS 100 ml).

Similarly, the processor 40 may be configured to provide a notification indicating to proceed with completing the order when the determination indicates that a prepared or returned medication is not available for completing the order. For example, if the order for the medication must be delivered to the delivery/drop location 60 within thirty minutes, and the estimated time to deliver a returned medication to the delivery/drop location 60 is one hour, then a notification on the output device 134 can indicate that the returned medication cannot be used for completing the order of the other medication. In certain aspects, the same notification or another notification can be provided by the processor 40 indicating the returned medication is expired, or the returned medication will expire within a threshold time period. The threshold time period may be based on an expiration time of the returned medication and an estimated amount of time for delivering the returned medication to the delivery/drop location 60.

The processor 40 is further configured to place the order in a virtual queue of orders to be filled. The order for medication from the medication database 45 is placed in a position in the virtual queue determined based on various factors. The factors affecting the position of an order for medication in the virtual queue include, for example, an estimated amount of time to prepare the medication, an estimated amount of time to deliver the medication to a delivery location (e.g., delivery/drop location 50), an estimated time at which the medication will be needed for administration to a patient at the delivery location, a delivery deadline for the medication, a degree of urgency for delivery of the medication, a type of the medication, or a component of the medication.

The order may be listed by the processor 40 at a position among other orders in the virtual queue where the order is provided with other orders of the same type (e.g., the same type of medication) or having a shared component. For instance, a new order for medication that requires a particular medication component for formulation can be grouped with other orders in the virtual queue that require the same particular medication component for formulation.

Such component based aggregation of medication orders may allow a healthcare facility, such as a hospital, to substantially minimize the amount of medication that is wasted when component medications are picked, or retrieved, by a healthcare professional, for the purposes of preparing ordered medications. For example, the processor 40 may provide, to a healthcare professional and for display on the output device 134, an indication of a container, or a set of containers, which provides a sufficient amount of the component medication to prepare the orders while minimizing any excess amount of the component medication, such as any amount of the component medication that is left unused after the ordered medications are prepared. The processor 40 thus minimizes the amount of component medications that is wasted when ordered medications are prepared. For example, the processor 40 may aggregate medication orders based on common component medications such that a healthcare professional can sequentially prepare ordered medications that have a common component medication. In this manner, the likelihood of any component medication being wasted, or expiring, is substantially minimized.

Accordingly, the processor 40 is configured to aggregate received orders into batches, or groups, for instance, based on the component medications that are indicated by each order for display in the queue. For example, the processor 40 may batch the orders such that orders that have a common (e.g., the same) component medication are picked together. After batching the orders, (e.g., based on the component medications), the processor 40 may select the first batch of orders and determine the containers from inventory (e.g., in the medication storage area 10) that should be picked to prepare the first batch of orders in a manner that minimizes wasted component medications. The containers may include vials, bags, bottles, packages, or generally any container that can store a component medication.

The processor 40 of the server 135 is further configured to execute instructions from the application 234 to determine a first batch of orders and provide an indication of the component medications needed to prepare the first batch, the amount of the component medications that needs to be retrieved for the first batch, and the containers from inventory that should be retrieved for the first batch. For example, the processor 40 may provide a user interface for display on the output device 134 to assist a healthcare professional with picking the component medications for the first batch. The healthcare professional may retrieve the containers from the inventory of the medication storage area 10 for preparing the first batch. For example, the healthcare professional may identify each container that is retrieved from inventory, (e.g., by scanning the containers with a bar code scanner 24). The processor 40 may transmit indications of the scanned containers to medication database 45, and the medication database 45 may store an indication that the containers are being removed from the inventory of the medication storage area 10 and being delivered to a temporary inventory of the preparation/fill area 20. The containers may then be delivered to the preparation/fill area 20 for preparation of the first batch of orders.

The processor 40 of the server 135 is further configured to execute instructions from the application 234 to receive an image or barcode identifying a component used to formulate the medication, and provide the image or barcode to a person, such as the pharmacist, responsible for verifying the medication is filled using the component. For example, during preparation of the package 70, a technician may place each component medication used to formulate the package 70 into a capture area of the prep/fill area 20 where the image recording device 25 or barcode reader 24 can capture a record (e.g., image or barcode reading) of each component medication being used. The processor 40 is configured to receive an input indicating the person has verified the medication has been filled using the component, and provide an indication that the order for the medication is ready for delivery to the patient. For example, the image or barcode reading of each component medication used to formulate the package 70 can be provided to a pharmacist in the pharmacy 1 or remote from the pharmacy 1 for review (e.g., as displayed on output device 134) and verification (e.g., using an input device 136 of the server 135) that the appropriate component medications were used to prepare the package 70. Upon verification by the pharmacist, the processor 40 indicates that the order is complete and that the package 70 for the order is ready for delivery.

In addition, once a medication is delivered, the processor 40 is further configured to receive notification or verification of whether the delivered medication is administered (or currently being administered) or unused. For example, the barcode of the medication may be scanned before being placed in an IV pump attached to a patient. An unused medication may be flagged or otherwise noted for relocation and possible reuse, as described herein.

The determination of the order in which to retrieve the unused package 70 can be based on various factors. For example, the determination can be based on an expiration date of the unused package 70. For instance, if the unused package will not expire for several days, then the determination may indicate that the unused package 70 may be retrieved towards the end of the ordered list. The determination can also be based on an estimated amount of time to retrieve the unused package 70. For instance, if it is estimated that it will take at least 15 minutes to retrieve the unused package 70, and the unused package 70 is set to expire within an hour, then the determination may indicate that the unused package 70 should be retrieved towards the beginning of the ordered list. The determination can further be based on a degree of urgency associated with the unused package 70. For instance, if the unused package 70 is listed as being required for delivery immediately ("stat" or "photostat"), then the determination may indicate that the unused package 70 should also be retrieved immediately.

The determination can also be based on a cost associated with the unused package 70. For instance, if the unused package 70 is very expensive to produce, and the expiration date of the unused package 70 is approaching, then the determination may indicate that the unused package 70 should also be retrieved immediately. The determination can yet further be based on an estimated distance to retrieve the unused package 70. The estimated distance can be calculated, for instance, based on a current location of a client 112, such as a mobile device client 112 carries by a delivery person 2. For instance, if two unused packages are to be retrieved, and a first unused package is closer to a current location of a mobile device client 112 of a delivery person 2 than a second unused package, then the determination can indicate that the first unused package should be retrieved first.

The determination can further be based on a likelihood of reuse of the unused package 70 or receipt of a new order for a medication that can be filled using the unused package 70. For instance, if the unused package 70 is for a frequently received order or can be used to fill a new order received at the pharmacy 1, then the determination can indicate that the unused package 70 should be retrieved.

In certain aspects, the determination is indicated by associating a priority value to each of the factors discussed above. As a result, various factors can be taken into consideration when generating a sum priority value indicating a priority in which to retrieve the unused package 70. The priority value can be based on the expiration date of the unused package 70, the estimated amount of time to retrieve of the unused package 70, the degree of urgency associated with the unused package 70, the cost associated with the unused package 70, and the estimated distance to retrieve of the unused package 70. For example, if the unused package expires in the next hour, this first factor may be assigned a high priority value, and if the estimated amount of time to retrieve the unused package is thirty minutes, then this second factor may also be assigned a high priority, thereby generating an even higher sum total priority value for retrieval of the unused package 70. The order of retrieving the unused packages can be sorted according to the priority values such that, for example, an unused package 70 having a higher priority value is retrieved prior to another unused package having a lower priority value.

The processor 40 of the server 135 also executes instructions from the application 234 to provide, for display, a listing of the unused medications based on the determined order for retrieving the unused medications. The listing can be displayed, for example, on a client 112. This may occur where, for example, the processor 40 of the server 135 sends over the network 150 instructions to a notification application 222 in a memory 220 of the client 112, and the notification application 222 instructs the processor 212 of the client 112 to display the listing on an output device 114 of the client 112. As an unused package 70 is retrieved, a barcode 72 of the unused package 70 can be scanned using the bar code reader 34 of the client 112, and a user can confirm that the unused package 70 has been retrieved using an input device 116 of the client. In certain aspects, the displayed listing can include a route to follow within the institution in order to retrieve each unused package 70 and return them to the delivery pickup area 30. The route can be provided, for example, via text instructions or via a visualization of a map of the institution. The visualization, which may be displayed on a mobile device client 112, can be updated based on a current location of the mobile device client 112.

In certain aspects, processor 40 of the server 135 also executes instructions from the application 234 to receive an identification of a first medication to be delivered to a first location and determine a route by which to deliver the first medication to the first location and retrieve at least one second medication at a second location. In certain aspects, the second location may be the same as the first location. The route is determined based on the first location, the second location, and at least one of an expiration date of the first or second medication, an estimated amount of time to deliver the first medication, an estimated amount of time to retrieve the second medication, a degree of urgency associated with each of the first and second medication, a cost associated with each of the first or second medication, and an estimated distance to retrieve each of the first and second medication. The processor 40 of the server 135 can provide, for display, the route for display on the client 112, such as a visualization on a mobile device client 112.

The processor 40 of the server 135 is also configured to execute instructions from the interface engine 335. The processor 40 is configured to interface with various devices, such as the electronic devices 130A-130F, as described herein, to reconcile incompatibility between the various data and parameters used by the electronic devices 130A-130F. By interfacing with the various electronic devices 130A-130F, the processor may better determine an efficient workflow by leveraging all available data, (e.g., inputs and outputs of each connected device). Although FIG. 3 shows the interface engine 335 as separate from the application 234, the interface engine 335 may be integrated with the application 234 or alternatively may call the application 234.

Figure 4A:
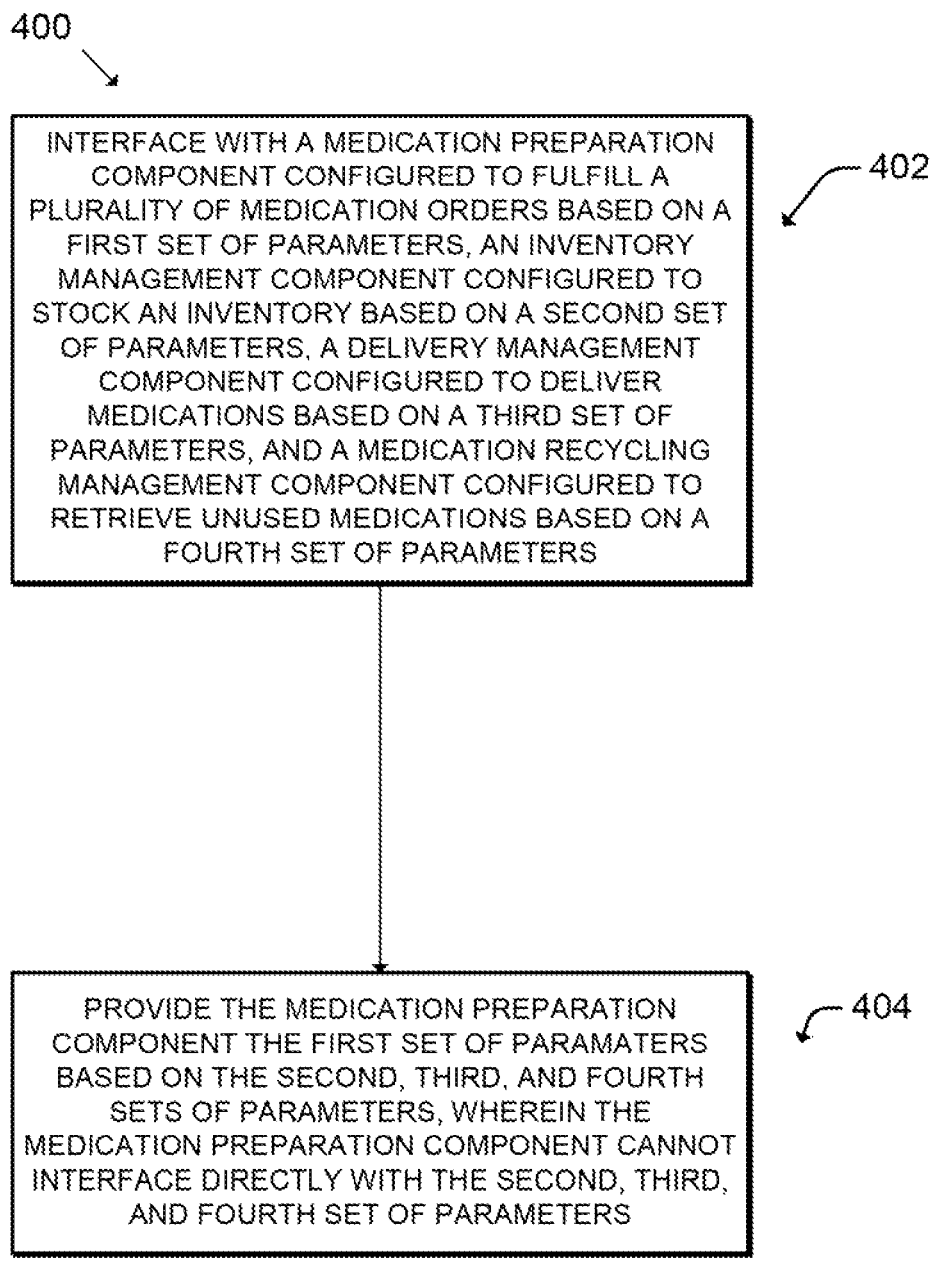
FIG. 4A is a flowchart of a process of interfacing between various devices according to example aspects of the present disclosure.

FIG. 4A illustrates a flowchart 400 of a process of an interface engine, such as the interface engine 335, which interfaces with various devices. At 402, the interface engine interfaces with (i) a medication preparation component configured to fulfill a plurality of medication orders based on a first set of parameters, (ii) an inventory management component configured to stock an inventory based on a second set of parameters, (iii) a delivery management component configured to deliver medications based on a third set of parameters, and (iv) a medication recycling management component configured to retrieve unused medications based on a fourth set of parameters. The medication preparation component is configured to fulfill a plurality of medication orders based on a first set of parameters, and may correspond to the electronic device 140B, such as a compounder as described herein. The inventory management component may be implemented in part, for example, with the server 115 or 135, as described herein. The delivery management component may be implemented in part, for example, with the server 115 or 135, as described herein. The medication recycling management component may be implemented in part, for example, with the server 115 or 135, as described herein.

At 404, providing the medication preparation component the first set of parameters based on the second, third, and fourth set of parameters, wherein the medication preparation component cannot interface directly with the second, third, and fourth set of parameters. For example, the inventory management component, delivery management component, and the medication recycling management component may be configured to utilize standardized data parameters as described herein. The compounder may utilize proprietary data parameters, which may not be compatible with the standardized parameters. The interface engine may reconcile the incompatibility, as described herein.

Figure 4B:
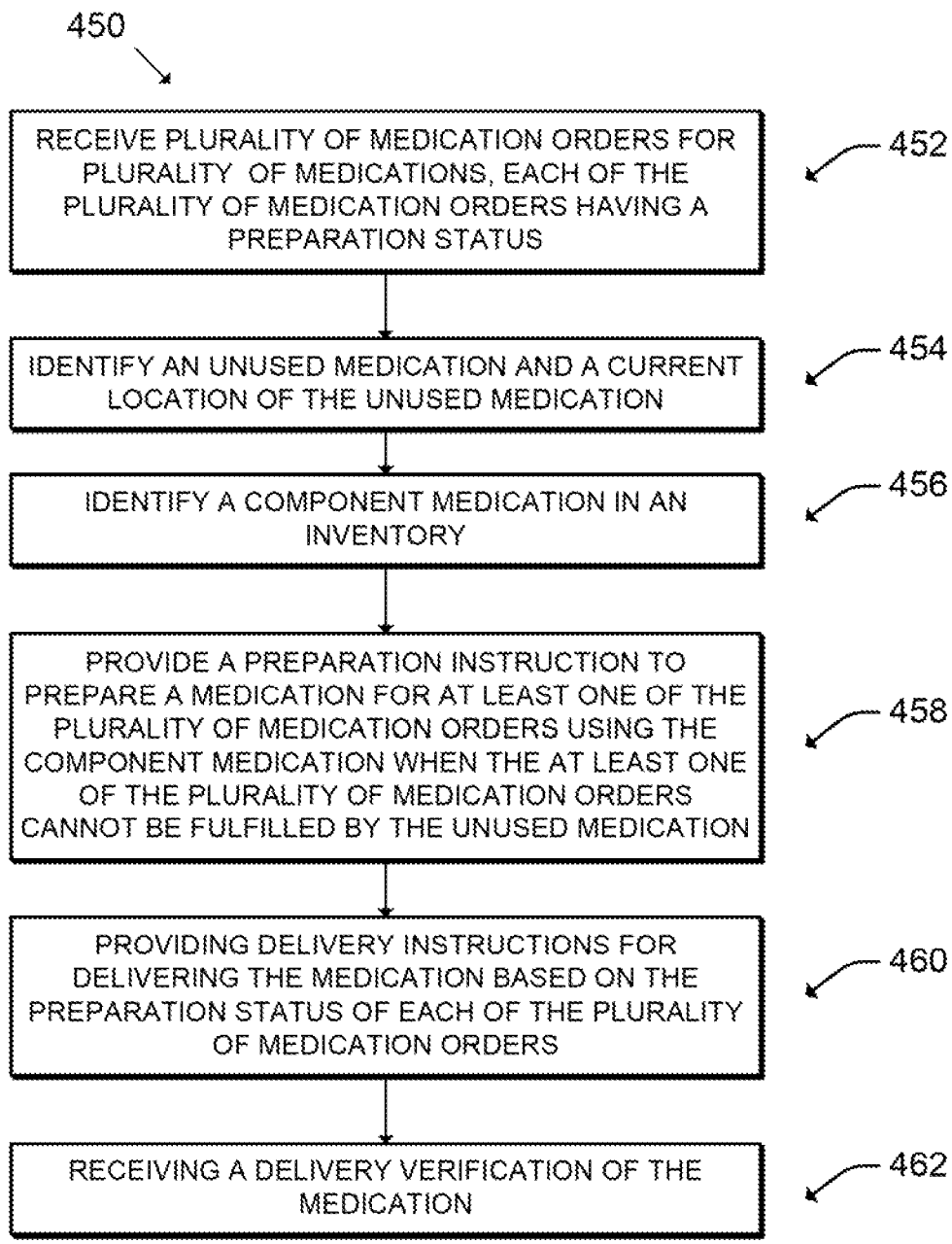
FIG. 4B is a flowchart of a process of managing medication workflow according to example aspects of the present disclosure.

FIG. 4B illustrates a flowchart 450 of managing a medication workflow using, for example, an interface engine, such as the interface engine 335 which may be implemented in part with the server 115 or 135, as described herein. In addition, the interface engine may perform the following steps directly, or through interfacing with the various components described above, which may include accessing other applications on the server 115 or 135. For example, the medication preparation component may perform a given step, using information provided from the medication recycling management component, facilitated through the interface engine. At 452, the interface engine receives a plurality of medication orders for a plurality of medications, each of the plurality of medication orders having a preparation status. At 454, the interface engine identifies an unused medication and a current location of the unused medication. At 456, the interface engine identifies a component medication in an inventory.

At 458, the interface engine provides a preparation instruction to prepare a medication for at least one of the plurality of medication orders using the component medication when the at least one of the plurality of medication orders cannot be fulfilled by the unused medication. For example, the interface engine may determine whether the unused medication can be used to fulfill the medication order by determining the expiration date of the unused medication, and whether the unused medication can be delivered and administered before the expiration date. The interface engine may further determine whether the unused medication can be used with a component medication or another unused medication to fulfill the medication order. The interface engine may further determine, based on delivery schedules and other related data, the availability of the unused medication, and may further determine whether a needed component medication is available in inventory or must be restocked. The interface engine may order additional component medications as needed, and factor in the delivery times of the additional component medications when determining availability. The interface engine may determine an efficient queue of preparation instructions based on such availability data. By interfacing with the various components or devices, the interface engine may utilize information which would normally not be available to each individual component.

At 460, the interface engine provides delivery instructions for delivering the medication based on the preparation status of each of the plurality of medication orders. At 462, the interface engine receives a delivery verification of the medication. The interface engine may perform the process through one or more devices, as described herein.

Figure 5:
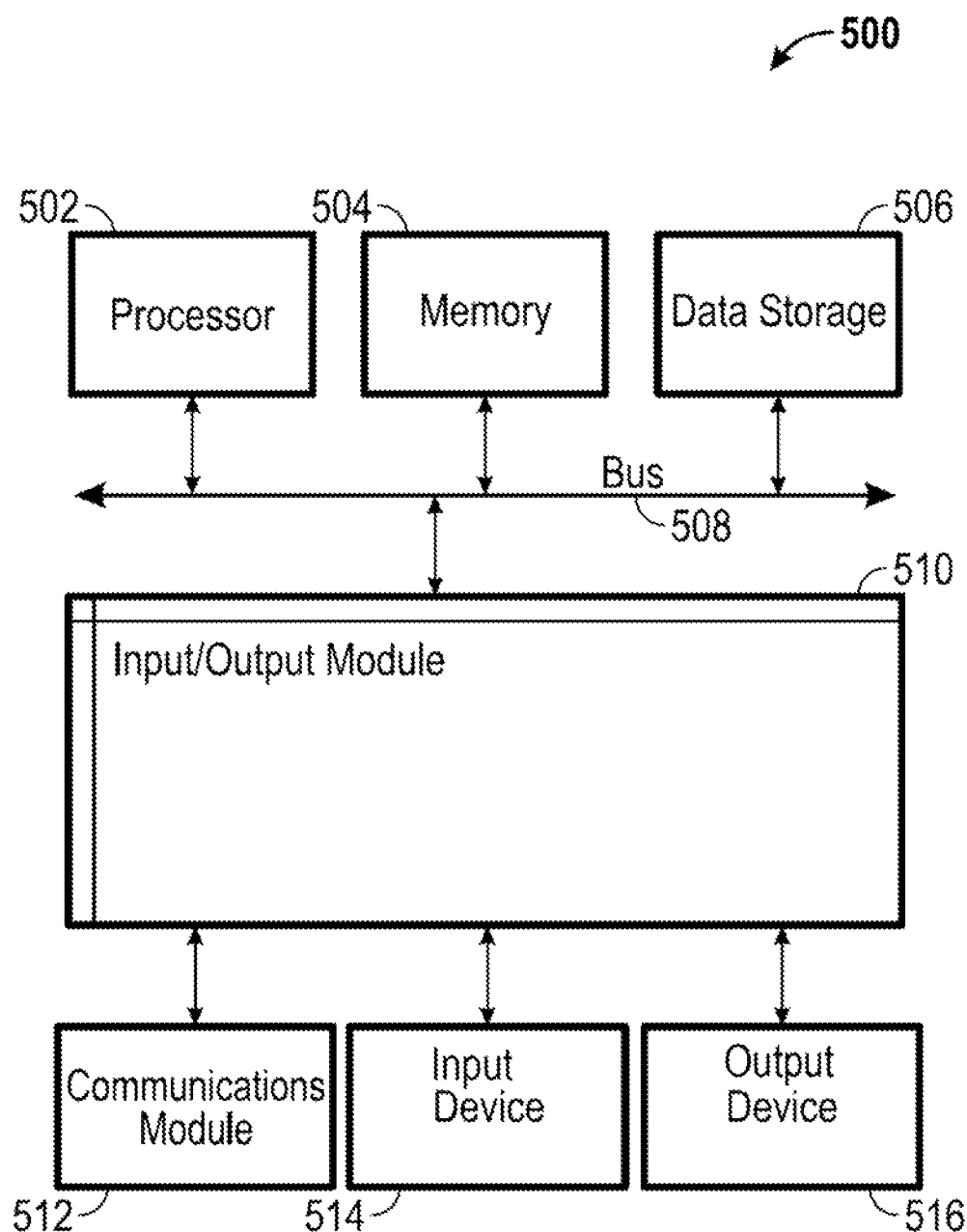
FIG. 5 is a block diagram illustrating an example computer system with which the client and server of FIG. 2 can be implemented.

FIG. 5 is a block diagram illustrating an example computer system 500 with which the client 112 and server 135 of FIG. 2 can be implemented. In certain aspects, the computer system 500 may be implemented using hardware or a combination of software and hardware, either in a dedicated server, or integrated into another entity, or distributed across multiple entities.

Computer system 500 (e.g., client 112 and server 135) includes a bus 508 or other communication mechanism for communicating information, and a processor 502 (e.g., processor 212 and 40) coupled with bus 508 for processing information. By way of example, the computer system 500 may be implemented with one or more processors 502. Processor 502 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 500 can include, in addition to hardware, code that creates an execution environment for the computer program in question, such as code that constitutes processor firmware, a protocol stack, a database management system, an operating system, or a combination of one or more of them stored in an included memory 504 (e.g., memory 220 and 232), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 508 for storing information and instructions to be executed by processor 502. The processor 502 and the memory 504 can be supplemented by, or incorporated in, special purpose logic circuitry.

The instructions may be stored in the memory 504 and implemented in one or more computer program products, i.e., one or more modules of computer program instructions encoded on a computer readable medium for execution by, or to control the operation of the computer system 500, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, embeddable languages, and xml-based languages. Memory 504 may also be used for storing temporary variable or other intermediate information during execution of instructions to be executed by processor 502.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 500 further includes a data storage device 506 such as a magnetic disk or optical disk, coupled to bus 508 for storing information and instructions. Computer system 500 may be coupled via input/output module 510 to various devices (e.g., barcode reader 34 and 24). The input/output module 510 can be any input/output module. Example input/output modules 510 include data ports such as USB ports. The input/output module 510 is configured to connect to a communications module 512. Example communications modules 512 (e.g., communications module 218 and 238) include networking interface cards, such as Ethernet cards and modems. In certain aspects, the input/output module 510 is configured to connect to a plurality of devices, such as an input device 514 (e.g., input device 116 and 136) and/or an output device 516 (e.g., output device 114 and 134). Example input devices 514 include a keyboard and a pointing device, (e.g., a mouse or a trackball), by which a user can provide input to the computer system 500. Other kinds of input devices 514 can be used to provide for interaction with a user as well, such as a tactile input device, visual input device, audio input device, or brain-computer interface device. For example, feedback provided to the user can be any form of sensory feedback, (e.g., visual feedback, auditory feedback, or tactile feedback); and input from the user can be received in any form, including acoustic, speech, tactile, or brain wave input. Example output devices 516 include display devices, such as a LED (light emitting diode), CRT (cathode ray tube), or LCD (liquid crystal display) screen, for displaying information to the user.

According to one aspect of the present disclosure, the client 112 and server 135 can be implemented using a computer system 500 in response to processor 502 executing one or more sequences of one or more instructions contained in memory 504. Such instructions may be read into memory 504 from another machine-readable medium, such as data storage device 506. Execution of the sequences of instructions contained in main memory 504 causes processor 502 to perform the process steps described herein. One or more processors in a multi-processing arrangement may also be employed to execute the sequences of instructions contained in memory 504. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, (e.g., as a data server), or that includes a middleware component, (e.g., an application server), or that includes a front end component, such as a client computer having a graphical user interface or a Web browser through which a user can interact with an implementation of the subject matter described in this specification, or any combination of one or more such back end, middleware, or front end components. The components of the system can be interconnected by any form or medium of digital data communication, (e.g., a communication network). The communication network (e.g., network 150) can include, for example, any one or more of a personal area network (PAN), a local area network (LAN), a campus area network (CAN), a metropolitan area network (MAN), a wide area network (WAN), a broadband network (BBN), the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computing system 500 can include clients and servers. A client and server are generally remote from each other and typically interact through a communication network. The relationship of client and server arises by virtue of computer programs running on the respective computers and having a client-server relationship to each other. Computer system 500 can be, for example, and without limitation, a desktop computer, laptop computer, or tablet computer. Computer system 500 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer readable medium" as used herein refers to any medium or media that participates in providing instructions or data to processor 502 for execution. Such a medium may take many forms, including, but not limited to, non-volatile media, volatile media, and transmission media. Non-volatile media include, for example, optical disks, magnetic disks, or flash memory, such as data storage device 506. Volatile media include dynamic memory, such as memory 504. Transmission media include coaxial cables, copper wire, and fiber optics, including the wires that comprise bus 508. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

This specification describes example aspects of the subject technology, which may include at least the following concepts:

Concept 1: A method of managing medications comprising: interfacing with (i) a medication preparation component configured to fulfill a plurality of medication orders based on a first set of parameters, (ii) an inventory management component configured to stock an inventory based on a second set of parameters, (iii) a delivery management component configured to deliver medications based on a third set of parameters, and (iv) a medication recycling management component configured to retrieve unused medications based on a fourth set of parameters; and providing the medication preparation component the first set of parameters based on the second, third, and fourth set of parameters, wherein the medication preparation component cannot interface directly with the second, third, and fourth set of parameters.

Concept 2: The method described in concept 1, wherein the medication preparation component comprises a compounder configured to prepare an intravenous (IV) medication.

Concept 3: The method described in concept 1, further comprising determining a common set of parameters corresponding to similar information of the first, second, third, and fourth sets of parameters.

Concept 4: The method described in concept 3, wherein the similar information corresponds to medication identification information.

Concept 5: The method described in concept 3, wherein the similar information corresponds to patient identification information.

Concept 6: The method described in concept 3, wherein the similar information corresponds to medication order identification information.

Concept 7: The method described in concept 3, wherein the medication preparation component directly interfaces with the common set of parameters.

Concept 8: The method described in concept 1, further comprising interfacing with an additional component based on a fifth set of parameters, wherein the medication preparation component cannot interface directly with the fifth set of parameters.

Concept 9: A method of managing medications comprising: receiving a plurality of medication orders for a plurality of medications, each of the plurality of medication orders having a preparation status; identifying an unused medication and a current location of the unused medication; identifying a component medication in an inventory; providing a preparation instruction to prepare a medication for at least one of the plurality of medication orders using the component medication when the at least one of the plurality of medication orders cannot be fulfilled by the unused medication; providing delivery instructions for delivering the medication based on the preparation status of each of the plurality of medication orders; and receiving a delivery verification of the medication.

Concept 10: The method described in concept 9, further comprising receiving a notification of whether the delivered medication is administered or unused.

Concept 11: The method described in concept 10, further comprising providing a return instruction for the unused delivered medication.

Concept 12: The method described in concept 11, further comprising: determining whether the unused delivered medication is reusable; identifying the unused delivered medication as another unused medication when it is determined to be reusable; and identifying the unused delivered medication as waste when it is determined not to be reusable.

Concept 13: The method described in concept 12, further comprising receiving a restock verification indicating the another unused medication is reusable.

Concept 14: The method described in concept 9, wherein providing the delivery instructions further comprises providing the delivery instructions based on a delivery deadline of each of the plurality of medication orders.

Concept 15: A non-transitory machine-readable medium containing machine-readable instructions for causing a processor to execute a method for managing medications, the method comprising: receiving a plurality of medication orders for a plurality of medications, each of the plurality of medication orders having a preparation status; identifying an unused medication and a current location of the unused medication; identifying a component medication in an inventory; providing a preparation instruction to prepare a medication for at least one of the plurality of medication orders using the component medication when the at least one of the plurality of medication orders cannot be fulfilled by the unused medication; providing delivery instructions for delivering the medication based on the preparation status of each of the plurality of medication orders; and receiving a delivery verification of the medication.

Concept 16: The method described in concept 15, further comprising receiving a notification of whether the delivered medication is administered or unused.

Concept 17: The method described in concept 16, further comprising providing a return instruction for the unused delivered medication.

Concept 18: The method described in concept 17, further comprising: determining whether the unused delivered medication is reusable; identifying the unused delivered medication as another unused medication when it is determined to be reusable; and identifying the unused delivered medication as waste when the it is determined not to be reusable.

Concept 19: The method described in concept 18, further comprising receiving a restock verification indicating the another unused medication is reusable.

Concept 20: The method described in concept 15, wherein providing the delivery instructions further comprises providing the delivery instructions based on a delivery deadline of each of the plurality of medication orders.

The subject matter of this specification has been described in terms of particular aspects, but other aspects can be implemented and are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. These and other implementations are within the scope of the following claims and contemplated in the disclosure herein.

What is claimed is:

1. A method of obtaining unused medications comprising:
   automatically receiving, from an infusion pump by a computing device, a replenishment signal indicating that an inter venous (IV) bag of a medication currently being administered by the infusion pump needs to be replenished;
   receiving, by the computing device, an automated notification indicating that an active tracking device affixed to a first unused medication currently designated for a second infusion pump was wirelessly scanned by an automated reader device at a current location of the first unused medication without a scanning action taken by a participant;
   identifying, by the computing device, responsive to receiving the replenishment signal from the infusion pump, the first unused medication, and the current location of the first unused medication based on the automated notification;
   determining, by the computing device, responsive to receiving the replenishment signal and identifying the first unused medication and the current location of the first unused medication, that a new medication order of the medication currently being administered by the infusion pump can be prepared using the first unused medication and a component medication in an inventory;
   responsive to receiving the replenishment signal and determining that the new medication order can be prepared using the first unused medication and the component medication:
      providing, by the computing device, a preparation instruction to prepare the new order of the medication currently being administered by the infusion pump using the component medication in the inventory and the first unused medication;
      determining, by the computer device, a current geolocation of a global positioning system (GPS) receiver of a mobile client device associated with a delivery person designated to retrieve a second unused medication within an area associated with the location of the first unused medication, the mobile client device being remote from the computing device;
      automatically determining, by the computer device, based on the current geolocation of the GPS receiver of the mobile device and the first and second unused medications, that the first unused medication is to be retrieved by the delivery person instead of the second unused medication;
      generating, by the computer device, a route to retrieve the first unused medication from the current location of the first unused medication and to deliver the first unused medication to the a delivery location associated with preparing the medication, instead of the second unused medication, based on the current location of the first unused medication and the current geolocation of the mobile client device associated with a delivery person designated to deliver within the area; and
      providing, by the computer device, to the mobile client device via an electronic network, the route and a delivery instruction to retrieve the first unused medication from the current location, instead of the second unused medication, and deliver the first unused medication to the delivery location associated with preparing the medication; and
   receiving, by the computing device after the delivery instructions are provided to the mobile client device, a delivery verification of the first unused medication.

2. The method of claim 1, wherein identifying the unused medication comprises receiving a notification of whether the delivered medication is administered or unused.

3. The method of claim 2, further comprising providing a return instruction for the unused delivered medication.

4. The method of claim 3, further comprising:
   determining whether the unused delivered medication is reusable;
   identifying the unused delivered medication as another unused medication when it is determined to be reusable; and
   identifying the unused delivered medication as waste when it is determined not to be reusable.

5. The method of claim 4, further comprising receiving a restock verification indicating the another unused medication is reusable.

6. The method of claim 1, wherein providing the delivery instructions further comprises providing the delivery instructions based on a delivery deadline of the new medication order.

7. A non-transitory machine-readable medium containing machine-readable instructions for causing a processor to execute a method for obtaining unused medications, the method comprising:
   automatically receiving, from an infusion pump, a replenishment signal indicating that an inter venous (IV) bag of a medication currently being administered by the infusion pump needs to be replenished;
   receiving an automated notification indicating that an active tracking device affixed to an first unused medication currently designated for a second infusion pump was wirelessly scanned by an automated reader device at a current location of the first unused medication without a scanning action taken by a participant;
   identifying, responsive to receiving the replenishment signal from the infusion pump, the first unused medication, and the current location of the first unused medication based on the automated notification;
   determining, responsive to receiving the replenishment signal and identifying the first unused medication and the current location of the first unused medication, that a new medication order of the medication currently being administered by the infusion pump can be prepared using the first unused medication and a component medication in an inventory;
   responsive to receiving the replenishment signal and determining that the new medication order can be prepared using the first unused medication and the component medication:
      providing a preparation instruction to prepare the new order of the medication currently being administered by the infusion pump using the component medication in the inventory and the first unused medication;

determining a current geolocation of a global positioning system (GPS) receiver of a mobile client device associated with a delivery person designated to retrieve a second unused medication within an area associated with the location of the first unused medication, the mobile client device being remote from the computing device;

automatically determining, based on the current geolocation of the GPS receiver of the mobile device and the first and second unused medications, that the first unused medication is to be retrieved by the delivery person instead of the second unused medication;

generating a route to retrieve the first unused medication from the current location of the first unused medication and to deliver the first unused medication to the a delivery location associated with preparing the medication based on the current location of the first unused medication and the current geolocation of the mobile client device associated with a delivery person designated to deliver within the area; and providing, to the mobile client device via an electronic network, the route and a delivery instruction to retrieve the first unused medication from the current location, instead of the second unused medication, and deliver the first unused medication to the delivery location associated with preparing the medication; and receiving, after the delivery instructions are provided to the mobile client device, a delivery verification of the first unused medication.

8. The non-transitory machine-readable medium of claim 7, wherein identifying the unused medication comprises receiving a notification of whether the delivered medication is administered or unused.

9. The non-transitory machine-readable medium of claim 8, wherein the method further comprises providing a return instruction for the unused delivered medication.

10. The non-transitory machine-readable medium of claim 9, wherein the method further comprises:
    determining whether the unused delivered medication is reusable;
    identifying the unused delivered medication as another unused medication when it is determined to be reusable; and
    identifying the unused delivered medication as waste when it is determined not to be reusable.

11. The non-transitory machine-readable medium of claim 10, wherein the method further comprises receiving a restock verification indicating the another unused medication is reusable.

12. The non-transitory machine-readable medium of claim 7, wherein providing the delivery instructions further comprises providing the delivery instructions based on a delivery deadline of the new medication order.

* * * * *